United States Patent [19]

Stone et al.

[11] Patent Number: 5,354,662

[45] Date of Patent: * Oct. 11, 1994

[54] MEASURING TISSUE BREAKDOWN PRODUCTS IN BODY FLUIDS

[75] Inventors: Phillip J. Stone, Chestnut Hill; Carl Franzblau, Newton, both of Mass.

[73] Assignee: Trustees of Boston University, Boston, Mass.

[*] Notice: The portion of the term of this patent subsequent to Jun. 8, 2010 has been disclaimed.

[21] Appl. No.: 30,680

[22] Filed: Mar. 11, 1993

Related U.S. Application Data

[63] Continuation-in-part of Ser. No. 523,587, May 15, 1990, Pat. No. 5,217,903.

[51] Int. Cl.$^5$ .................. C12Q 1/00; G01N 33/53
[52] U.S. Cl. .................. 435/7.92; 436/57; 436/161; 436/504; 436/536; 436/542
[58] Field of Search .................. 436/57, 63, 87, 89, 436/161, 177, 538, 536, 811, 542, 516, 515, 504; 530/395; 435/7.92, 7

[56] References Cited

U.S. PATENT DOCUMENTS

| | | |
|---|---|---|
| 4,312,853 | 1/1982 | Timpl . |
| 4,628,027 | 12/1986 | Gay .................. 435/7 |
| 4,778,768 | 10/1988 | Heingard et al. .................. 436/501 |
| 4,857,456 | 8/1989 | Urist .................. 435/7 |
| 5,011,608 | 4/1991 | Damjanovic .................. 210/656 |
| 5,140,103 | 8/1992 | Eyre .................. 530/327 |
| 5,217,903 | 6/1993 | Stone et al. .................. 436/57 |
| 5,252,461 | 10/1993 | Weisbart .................. 435/7.92 |
| 5,264,370 | 11/1993 | Aken et al. .................. 436/501 |

FOREIGN PATENT DOCUMENTS

WO89/12824 12/1989 PCT Int'l Appl. .

OTHER PUBLICATIONS

Van Eijk, H., et al., "3-Methylhistidine Determined in Plasma by High-Performance Liquid Chromatography", 1990, Clinical Chemistry, vol. 36, No. 3, pp. 556-559.

Long, C., et al., "Urinary Excretion of 3-Methylhistidine: An Assessment of Muscle Protein Catabolism in Adult Normal Subjects and During Malnutrition, Sepsis, and Skeletal Trauma", Aug. 1981, Metabolism, vol. 30, No 8, pp. 765-776.

Hu, C., et al., "Synthesis and Turnover of Protein-Bound N$^t$-Methylhistidine in Cultured Vascular Smooth Muscle Cells", 1985, Surv. Synth. Path. Res., vol. 4, pp. 380-388.

Heinegard, D., et al., "Determination of Serum Creatinine by a Direct Colorimetric Method", 1973, Clin. Chem. Acta., vol. 43, pp. 305-310.

Davies, S., et al., "Urine Desmosine is Unrelated to Cigarette Smoking or to Spirometric Function", 1983, Am. Rev. Respir. Dis., pp. 473-475.

Pelham, F., et al., "Urinary Excretion of Desmosine (Elastin Cross-Links) in Subjects with PiZZ Alpha-1-Antitrypsin Deficiency, a Phenotype Associated (List continued on next page.)

*Primary Examiner*—Nina Bhat
*Attorney, Agent, or Firm*—Choate, Hall & Stewart

[57] ABSTRACT

A method for determining the quantity of a connective tissue or muscle tissue breakdown product in a body fluid from an animal includes steps of providing a standard comprising the breakdown product having a label, the standard having a known specific activity, combining the standard and a sample of the body fluid, removing from the combined standard and sample a purified breakdown product fraction containing labelled breakdown product from the standard together with breakdown product from the sample, and measuring the specific radioactivity of the fraction as a measure of the quantity of the breakdown product in the sample. Also, methods for assessing, in a body fluid from an animal, the condition of a selected connective tissue or a muscle tissue in an animal, and for assessing a disease process that includes destruction of a specified connective tissue component or muscle tissue, and for assessing the efficacy of a therapy for treatment of such a disease process, include the steps of the method for determining the quantity of a tissue breakdown product.

43 Claims, 12 Drawing Sheets

OTHER PUBLICATIONS with Hereditary Predisposition to Pulmonary Emphysema[1-3]", 1985, Am. Rev. Respir. Dis., vol. 132, pp. 821-823.

Strongin, et al., "Determination of the Elastin Content of Tissues by Measuring Desmosine and Isodesmosine", 1977. Anal. Biochem., vol. 79, pp. 11-15.

Thomas, et al., "Degradation Products from Elastin", Nov. 1963, Nature, vol. 200, No. 4907, pp. 651-652.

Lansing, A., et al., "The Structure and Chemical Characterization of Elastic Fibers as Revealed by Elastase and by Electron Microscopy[1]", 1952 Anat. Rec., vol. 114, pp. 555-570.

Moore, S., et al., "Photometric Ninhydrin Method For Use in the Chromatography of Amino Acids", 1948, J. Biol. Chem., vol. 176, pp. 367-388.

Barone, L., et al., "Alteration of the Extracellular Matrix of Smooth Muscle Cells by Ascorbate Treatment", 1985, Biochimica et Biophysica Acta, vol. 840, pp. 245-254.

Yamaguchi, Y., et al., "High-Performance Liquid Chromatographic Determination of Desmosine and Isodesmosine in Tissues and its Application to Studies of Alteration of Elastin Induced by Atherosclerosis", 1987, J. Chromat., vol. 422, pp. 53-59.

Kuhn, C., et al., "Degradation of Elastin in Experimental Elastase-Induced Emphysema Measured by a Radioimmunoassay for Desmosine", 1983, Exp. Lung. Res., vol. 5, pp. 115-123.

Stone, P., et al., "Elastin in a Neonatal Rat Smooth Muscle Cell Culture Has Greatly Decreased Susceptibility to Proteolysis by Human Neutrophil Elastase. An In Vitro Model of Elastolytic Injury", 1987, In Vitro Cell. & Dev. Biol., vol. 23, No. 10, pp. 663-ff.

Harel, S., et al., "Desmosine Radioimmunoassay for Measuring Elastin Degradation In Vivo", 1980, Am. Rev. Resp. Dis., vol. 122, pp. 769-773.

Goldstein, R., et al., "Urinary Excretion of Elastin Peptides Containing Desmosine after Intratracheal Injection of Elastase in Hamsters", 1978, J. Clin. Invest., vol. 5, pp. 1286-1290.

Fujimoto, D., et al., "Analysis of Pyridinoline, a Cross-Linking Compound of Collagen Fibers, in Human Urine[1]", 1983, J. Biochem., vol. 94, pp. 1133-1136.

Black, D., et al., "Quantitative Analysis of the Pyridinium Crosslinks of Collagen in Urine Using Ion-Paired Reversed-Phase High-Performance Liquid Chromatography", 1987, Analytical Biochem., vol. 169, pp. 197-203.

Laurent, P., et al., "Quantitation of Elastin in Human Urine and Rat Pleural Mesothelial Cell Matrix by a Sensitive Avidin-Biotin ELISA for Desmosine", 1988, J. Immunological Methods, vol. 107, pp. 1-11.

Starcher, B., "Determination of the Elastin Content of Tissues by Measuring Desmosine and Isodesmosine", 1977, Anal. Biochem., vol. 79, pp. 11-15.

Stone, P., et al., "Induction and Exacerbation of Emphysema in Hamsters with Human Neutrophil Elastase Inactivated Reversibly by a Peptide Boronic Acid", 1990, Am. Rev. Respir. Dis., vol. 141, pp. 47-52.

Beardsworth, L., et al., "Changes with Age in the Urinary Excretion of Lysyl-and Hydroxylysylpyridinoline, Two New Markers of Bone Collagen Turnover", 1990, J. Bone, etc., vol. 5, No. 7, pp. 671-676.

Gunga-Smith, Z., et al., "Content of the Collagen and Elastin Cross-Links Pyridinoline and the Desmosines in the Human Uterus in Various Reproductive States", 1985, Am. J. Obstet. Gynecol., vol. 153, pp. 92-95.

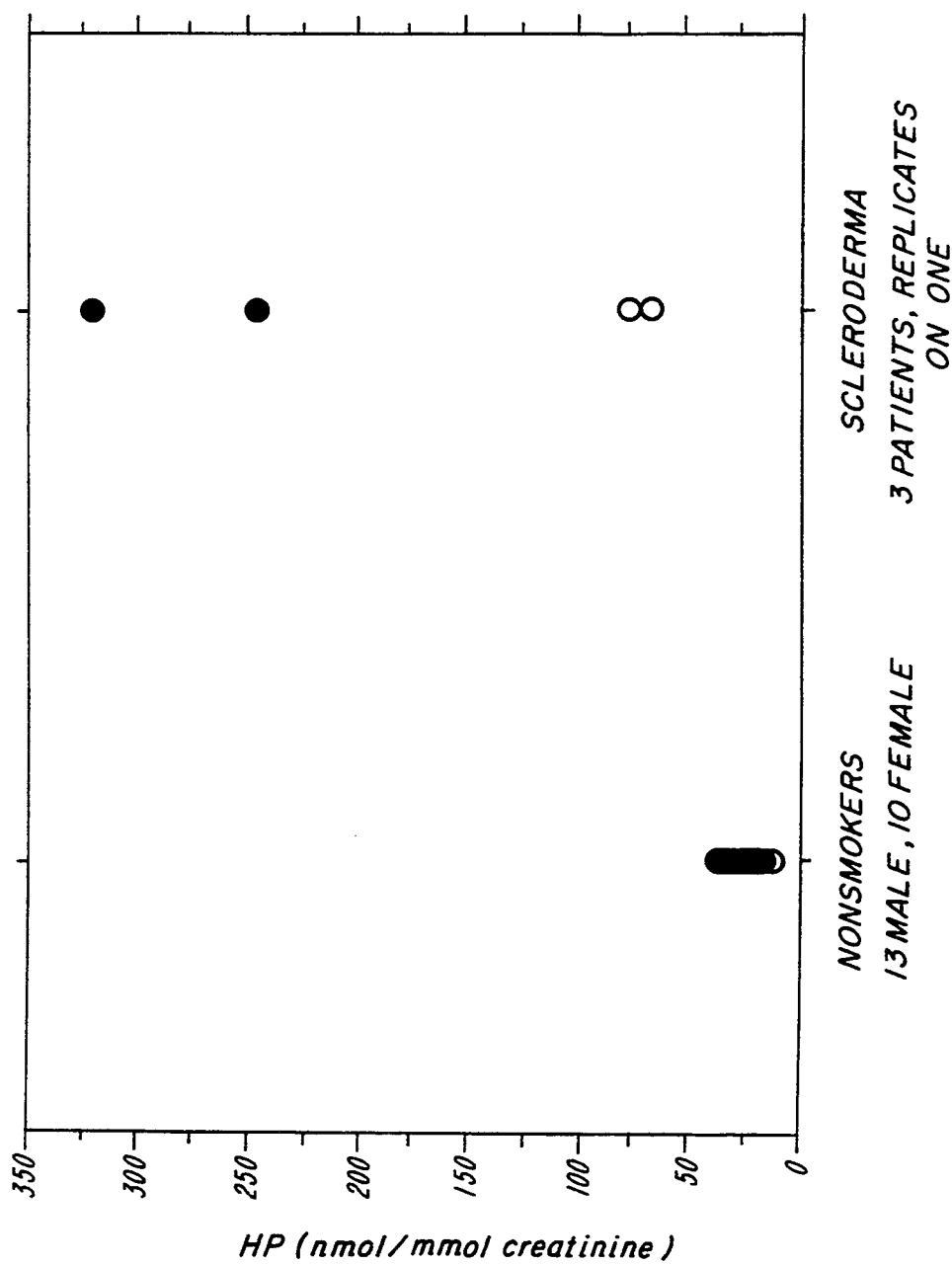

MEASURING TISSUE BREAKDOWN PRODUCTS IN BODY FLUIDS

This invention was made in the course of work supported in part by funds provided by the U.S. Government, and the Government has certain rights in the invention.

This application is a continuation-in-part of the copending application U.S. Ser. No. 523,587, filed on May 15, 1990, now U.S. Pat. No. 5,217,903.

BACKGROUND OF THE INVENTION

This invention relates to measuring connective tissue breakdown products and muscle tissue breakdown products in a body fluid from an animal.

A breakdown of crosslinked fibrous elastin and crosslinked fibrous collagen, hereafter referred to as elastin and collagen or connective tissue components, is believed to be involved in the pathogenesis of some chronic diseases. In chronic obstructive pulmonary disease and in cystic fibrosis, for instance, the elastase and neutrophil load in the lungs is increased, and elastin and collagen destruction in the lungs is believed to be an ongoing part of the disease process. Also, the proteolytic digestion of lung elastin is thought to be a primary event of the alveolar wall destruction that occurs in the pathogenesis of pulmonary emphysema.

Desmosine and isodesmosine are cross-linking amino acids present in elastin. Because desmosine and isodesmosine are unique to elastin, they are recognized as established specific markers for crosslinked fibrous elastin and elastin degradation products in mammalian tissues and fluids. Moreover, desmosine and isodesmosine are not metabolized, and are passed directly to the urine, and for these reasons, some attempts to monitor elastin breakdown products as an indication of the condition of the alveolar walls have been directed to measuring urinary desmosine.

Measurements of urinary desmosine by means of radioimmunoassay have to date failed to support an elastase-antielastase hypothesis of emphysema, suggesting to some workers that the monitoring of elastin degradation products does not provide an indication of disease processes that effect elastin breakdown.

Pyridinoline and deoxypyridinoline are cross-linking amino acids present in collagen. Pyridinoline and deoxypyridinoline are used as specific markers for collagen and for collagen degradation products because they are unique to collagen, and they are not metabolized but are passed directly to the urine.

A breakdown of muscle tissue is believed to be involved in some pathologic conditions, and a decrease in the quantity of muscle breakdown components is believed to be a component of protein-calorie malnutrition. Catabolism of muscle protein results in the excretion of 3-methylhistidine, also known as N-methylhistidine in the urine. Measurement of 3-methylhistidine in the urine can provide an assessment of muscle protein breakdown, since the major source of 3-methylhistidine in the body fluids is from the muscle proteins, actin and myosin.

SUMMARY OF THE INVENTION

We have discovered a sensitive quantitative assay for connective tissue breakdown products, particularly for cross-linking amino acids, and for muscle tissue breakdown products, particularly for 3-methylhistidine. The assay includes an isotope dilution step using isotopically labelled breakdown products. The quantity of connective tissue breakdown products, desmosine and isodesmosine from elastin and pyridinoline and deoxypyridinoline from collagen, and the muscle tissue breakdown product 3-methylhistidine, can be determined in a body fluid by combining at least one of the labelled breakdown products with the body fluid sample, followed by column chromatography to prefractionate the sample to remove interfering contaminants, and to concentrate the sample with respect to the desired amino acids. The quantities of each breakdown product are determined using high performance liquid chromatography or amino acid analysis in conjunction with scintillation counting, or using a radio-immunoassay "RIA" or a enzyme-linked immunosorbent assay "ELISA" in conjunction with liquid scintillation counting, or using mass spectrometry or infra-red absorption spectroscopy. The inclusion of an isotope dilution step provides an internal control which minimizes problems that can arise from variation in recovery during the assay, as will be described in more detail below.

In general, in one aspect, the invention features a method for determining at least one of a connective tissue breakdown product and a muscle tissue breakdown product in a body fluid from an animal (a human or non-human animal), including steps of providing a standard including the breakdown product having an isotopic label at a known specific activity, in which the label can be radioactive or stable, combining the standard with a sample of the body fluid, substantially purifying from the combined standard and sample a purified breakdown product fraction containing labelled breakdown product from the standard together with breakdown product from the sample, and measuring the quantity of breakdown product and the quantity of labelled breakdown product in the substantially purified breakdown product fraction.

In preferred embodiments the substantially purifying step includes treating the combined standard and sample by chromatography, more preferably by gel permeation chromatography, such as by column chromatography using Sephadex, which is a dextran gel (Pharmacia). Most preferably the substantially purifying step includes treating the combined standard and sample by gel permeation chromatography with a dextran gel having an exclusion volume corresponding to approximately 1,500 daltons, such as by column chromatography using Sephadex G-15, which is a dextran gel having an exclusion volume corresponding to approximately 1,500 daltons.

In preferred embodiments the measuring step includes using high performance liquid chromatography or amino acid analysis or an RIA or an ELISA to measure the quantity in the fraction of the labelled breakdown product and the breakdown product from the sample, and using liquid scintillation counting to measure the quantity of label in the breakdown product fraction. In preferred embodiments the measuring step includes using mass spectrometry or infrared absorption spectroscopy to separately quantitate the amount of purified breakdown product from the sample and the amount of purified isotopically labelled breakdown product.

In preferred embodiments, the connective tissue breakdown product is desmosine and the labelled breakdown product is isotopically labelled desmosine, or the connective tissue breakdown product is isodesmosine and the labelled breakdown product is isotopically labelled isodesmosine, or the connective tissue breakdown product is pyridinoline and the labelled breakdown product is isotopically labelled pyridinoline, or the connective tissue breakdown product is deoxypyridinoline and the labelled breakdown product is isotopically labelled deoxypyridinoline, or the muscle tissue breakdown product is 3-methylhistidine and the labelled breakdown product is isotopically labelled 3-methylhistidine.

In another aspect, the invention features a method for determining a plurality of tissue breakdown products from at least one of connective tissue and muscle tissue, in a body fluid from an animal, including steps of providing a standard including at least one of the breakdown products having an isotopic label at a known specific activity, combining the standard with a sample of the body fluid, substantially purifying from the combined standard and sample a purified breakdown product fraction containing labelled breakdown product from the standard together with breakdown products from the sample, and measuring the quantity of breakdown products and the quantity of labelled breakdown products in the substantially purified breakdown product fraction.

In preferred embodiments the plurality of tissue breakdown products is selected from the group consisting of desmosine, isodesmosine, pyridinoline, deoxypyridinoline, and 3-methylhistidine. In preferred embodiments the standard(s) is selected from the group consisting of desmosine, isodesmosine, pyridinoline, deoxypyridinoline, and 3-methylhistidine.

In another aspect, the invention features a method for assessing, in a body fluid of an animal, a condition of a selected connective tissue, including steps of providing a standard including a breakdown product having a radioactive or stable isotopic label at a known specific activity, combining the standard with a sample of the body fluid, substantially purifying from the combined standard and sample a purified breakdown product fraction containing labelled breakdown product from the standard together with breakdown product from the sample, and measuring the quantity of breakdown product and the quantity of labelled breakdown product in the substantially purified breakdown product fraction, in which the breakdown product is known to result from breakdown of the selected connective tissue. "Assessing", as that term is used herein, means the method of the invention can be used for the diagnosis of a disease and for monitoring the progress of a disease.

In preferred embodiments the selected connective tissue contains elastin, or contains collagen, or contains both elastin and collagen.

In another aspect, the invention features a method for assessing, in a body fluid of an animal, a condition of a selected muscle tissue in an animal, including steps of providing a standard including the breakdown product having a radioactive or stable isotopic label at a known specific activity, combining the standard with a sample of the body fluid, substantially purifying from the combined standard and sample a purified breakdown product fraction containing labelled breakdown product from the standard together with breakdown product from the sample, and measuring the quantity of breakdown product and the quantity of labelled breakdown product in the substantially purified breakdown product fraction. In which the breakdown product is known to result from breakdown of the selected muscle tissue.

In another aspect, the invention features a method for assessing, in a body fluid of an animal, a disease process that includes destruction of a specified tissue component, including at least one of a connective tissue component and a muscle tissue component, including steps of providing a standard including the breakdown product having a radioactive or stable isotopic label at a known specific activity, combining the standard with a sample of the body fluid, substantially purifying from the combined standard and sample a purified breakdown product fraction containing labelled breakdown product from the standard together with breakdown product from the sample, and measuring the quantity of breakdown product and the quantity of labelled breakdown product in the substantially purified breakdown product fraction.

In another aspect, the invention features a method for assessing, in a body fluid of an animal, the efficacy of a therapy for treatment of a disease process that includes destruction of at least one of a specified connective tissue component and a specified muscle tissue component, including steps of providing a standard including the breakdown product having a radioactive or stable isotopic label at a known specific activity, combining the standard with a sample of the body fluid, substantially purifying from the combined standard and sample a purified breakdown product fraction containing labelled breakdown product from the standard together with breakdown product from the sample, and measuring the quantity of breakdown product and the quantity of labelled breakdown product in the substantially purified breakdown product fraction.

The disease process can be, for example, a disease process of chronic obstructive pulmonary disease, or of cystic fibrosis; or of acute respiratory distress syndrome, or of lung emphysema due to a genetic deficiency of alpha-1-antitrypsin, or of metastatic tumors of the lung, in which elastin breakdown may occur; or an autoimmune disease process such as rheumatoid arthritis or systemic lupus erythematosus; or a disease process of a skin disorder, such as scleroderma, or of a degenerative skin disorder, in which elastin breakdown and/or collagen breakdown may occur; or a disease process of arthritis, in which breakdown of collagen to release pyridinoline may occur, or of a bone disease such as Paget's disease or osteoarthritis or osteoporosis, in which breakdown of bone collagen to release deoxypyridinoline and pyridinoline may occur; or a disease process of fibrosis of the lung or liver; or a disease process of inflammation of the blood vessels; or a disease process of muscle atrophy, or of sepsis, or of thermal trauma; or a normal process of pregnancy, or an abnormal process of pregnancy that indicates impending premature termination of pregnancy.

The invention provides a highly sensitive quantitative assay for specific products of connective tissue breakdown, yielding results comparable to or better than those achieved by amino acid analysis. The invention provides a highly sensitive quantitative assay for specific products of muscle tissue breakdown. The method includes the principle that a decrease in specific activity of the added isotopically labelled tissue breakdown product is proportional to the quantity of the endogenous product in the original sample, and the amount of change of the specific activity of added isotopically labelled breakdown product can be used to quantitatively determine the total amount of breakdown product present in the original sample. The specific activity of the labelled product in the sample remains unchanged during purification steps, so that values derived by the method are independent of the level of recovery of the material being measured. This permits treatment of the sample in a multistep procedure in which recovery levels can vary.

DESCRIPTION OF PREFERRED EMBODIMENTS

Drawings

FIGS. 5A and 5B are graphs of the urinary desmosine and pyridinoline ("HP") concentrations, respectively, for individuals who are non-smokers and individuals who suffer from scleroderma. The quantities of these breakdown product have been normalized using urinary creatinine concentration.

STRUCTURE OF THE ASSAY

Figure 1:
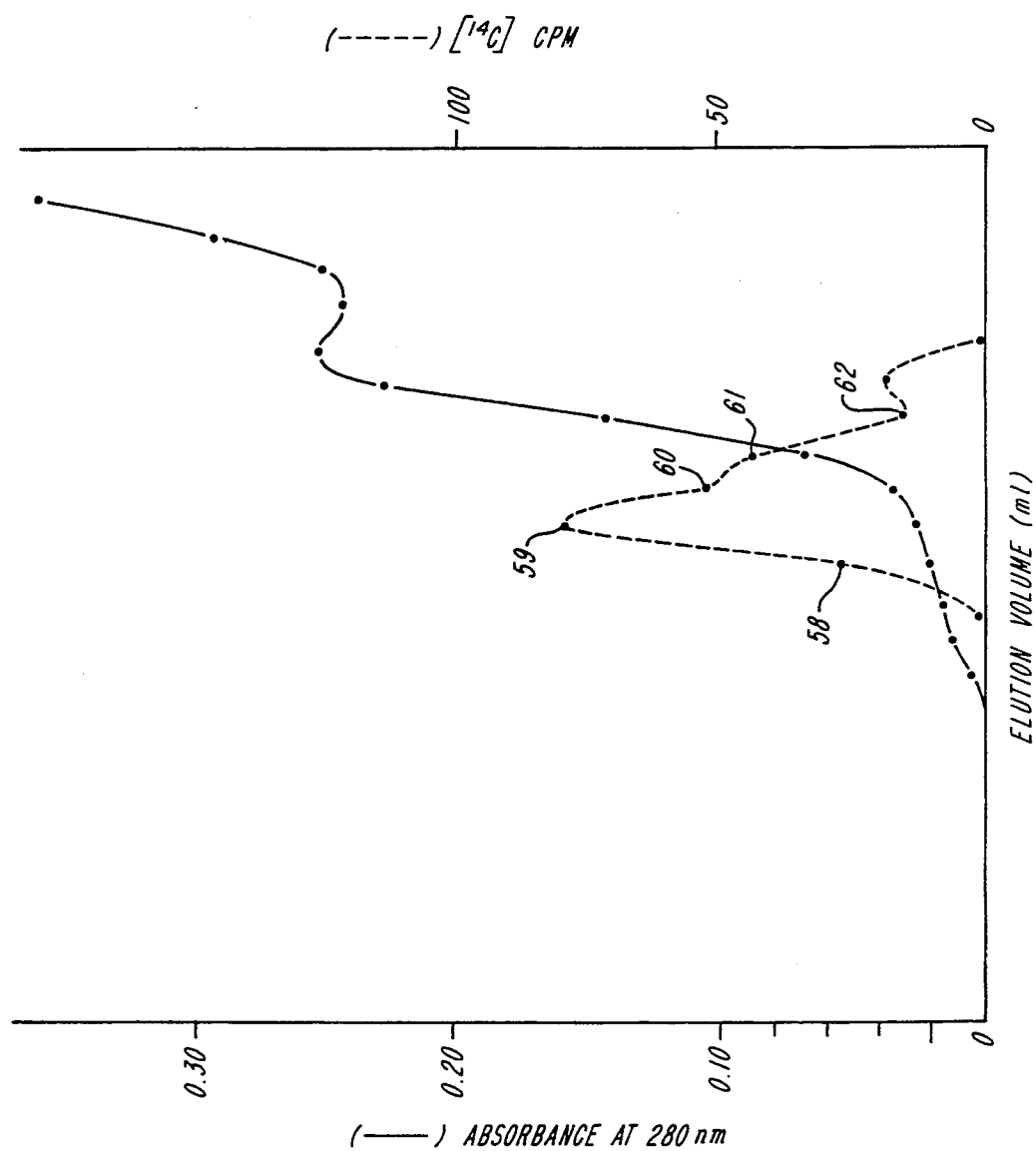
FIG. 1 is a chromatogram of a hydrolyzed human urine sample combined with $^{14}$C-desmosine ("$^{14}$C-DES").

Generally, the assay according to the invention includes steps of combining a standard that contains a selected labelled connective tissue breakdown product or a muscle tissue breakdown product at a known specific activity with a sample of the body fluid to be assayed, purifying a fraction from the sample that contains both breakdown product from the sample and labelled breakdown product from the standard, and measuring the quantity of breakdown product and the quantity of labelled breakdown product in the purified fraction. The difference in the quantity of label in the purified fraction and in the known quantity of label added to the sample provides a measure of the loss of breakdown product during the purifying step, and can be used to determine the original amount of breakdown product in the sample.

Preparation of Labelled Desmosine and Isodesmosine

DES and isodesmosine ("IDES") were prepared from neonatal rat smooth muscle cell cultures generally as described in Stone et al. (1987). This preparation method can be used for radioactive or stable isotope labelled DES and IDES, for example $^{14}$C or $^{2}$H. The procedure to label with either isotope is the same, namely cells are fed with isotopically labelled lysine or with another labelled metabolite that can be converted biosynthetically into the crosslinking amino acids.

For example, 1 week old T-75 flasks containing first passage cells were pulsed in the presence of serum for 24 h by addition of $^{14}$C(U)-lysine (20 $\mu$Ci per flask) (New England Nuclear), after which the medium was poured off and the cultures were refed. Five weeks later the cell layers were harvested by scraping and homogenized, and elastin was isolated by a hot alkali procedure generally as described in A. I. Lansing et al. (1952, *Anat. Rec.*, Vol. 114, pp. 555-570). The residue was hydrolyzed in 6N HCl at 110° C. for 24 h in vacuo.

The presence of labelled DES and IDES was verified by loading an aliquot of the hydrolysate onto a Beckman Model 119 CL amino acid analyzer. The eluted material was collected in 0.5 min fractions and assessed for radioactivity by liquid scintillation spectrometry, using quench correction factors as appropriate. The amino acid composition of the residue exhibited the composition of elastin described in Barone et al. (1985, *Biochim. Biophys. Acta*, Vol. 840, pp. 245-254). DES and IDES eluted 4 min apart at 99 and 95 min, respectively. Four lysine color equivalents were used to calculate the amount of DES and IDES present. DES plus IDES composed 0.20% of the amino acids present in the elastin. The specific radioactivity of DES and IDES were respectively 776 and 836 cpm/nmol (80% efficiency) in Ultima Gold scintillation cocktail (Packard Instruments). These values have been increase by 17% to correct for the loss of four radiolabelled carbon atoms from both DES and IDES as carbon dioxide upon reaction with ninhydrin (see, S. Moore et al., 1948, Jour. Biol. Chem., Vol. 176, pp. 367-388).

The labelled DES and IDES was purified in larger aliquots of 4 mg on the amino acid analyzer. The eluted material was not reacted with ninhydrin. Fractions were collected and assessed for radioactivity, and fractions containing DES or IDES were pooled. This procedure was repeated. The specific radioactivity of the pooled material was confirmed by loading small aliquots on the amino acid analyzer, allowing the eluted material to react with ninhydrin and the ninhydrin-reactive material was assessed for radioactivity as described above. Quantification of DES and IDES was confirmed using nonradioactive DES and IDES. The concentration of solutions containing DES or IDES was confirmed spectrophotometrically (see, J. Thomas et al. (1963), *Nature*, No. 4907, p. 651). When nonradioactive DES and IDES, in amounts respectively of 1.07 and 1.13 nmol, were loaded on the amino acid analyzer, 1.05 and 1.08 nmol, respectively, were recovered.

Preparation of Labelled Pyridinoline and Deoxypyridinoline

Either radioactive or stable isotope labelled pyridinoline ("HP") and deoxypyridinoline ("LP") can be made using isotope labelled lysine as a precursor or using another labelled metabolite that can be converted biosynthetically into the crosslinking amino acids. Briefly, labelled HP and LP can be made according the method provided above for DES and IDES, except that the collagen is prepared from the cells that have been grown as layers in the presence of sodium ascorbate (to increase the production of collagen by the cells), and elastase, porcine pancreatic elastase for example, and trypsin are used to digest the collagen. The cells are scraped from the growth surface, homogenized and incubated with the elastase (1:100 weight ratio of elastase to substrate) and the trypsin (1:1000 weight ratio) at 33° C. for 16 hr in 0.03M $Na_2CO_3$, pH 8.8 and 0.01% $NaN_3$. This was then centrifuged at 30,000×g for 20 min. the pellet was washed with water at 4° C. and centrifuged again. The prepared labelled collagen is hydrolyzed in hot acid as above, and analyzed by amino acid analysis as described above. Leucine color equivalents were used to calculate the amount of HP and LP present as described by Gunga-Smith et al. (1985, Am. Jour. Obstet. Gynecol., Vol. 153, pp. 92–95), and incorporated herein by reference. Labelled HP and LP can be purified for use as a standard according to the method described for DES and IDES above, or by HPLC as described below.

Preparation of Labelled 3-methylhistidine

Radioactive or stable isotopically labelled 3-methylhistidine ("3-MH") can be prepared from cultured rabbit aortic smooth muscle cells ("rabbit SMC") that have been fed isotopically labeled histidine (Hu et al., 1985, Surv. Synth. Path. Res., Vol. 4, pp. 380–388). Briefly, rabbit SMC cultures in T-75 flasks were fed with fresh medium 24 h before pulsing with isotopically labelled histidine. The cells were washed with calcium- and magnesium- free Puck's saline G solution then incubated in a serum-free medium lacking histidine for 2 h at 37° C. This medium was then replaced with medium containing isotopically labelled histidine, for example $^{14}C$-histidine (0.7 µCi/ml of medium). The cells were incubated for 22 h in a 5% $CO_2$:95% air humidified incubator at 37° C., and then harvested. The cells were harvested by placing scraping the flasks on ice and then lyophilizing the cell suspension. The lyophilized cells were hydrolyzed in vacuo in 6M HCl at 110° C. for 44 h, and evaporated to dryness. An aliquot was dissolved in 0.01N HCl, applied to an amino acid analyzer (Beckman model 119 CL), and fractions were collected. The radioactivity of the collected fractions was determined by liquid scintillation counting. Labelled histidine was separated from labelled 3-MH using a lithium citrate buffer, as described for physiological systems (Beckman 118/119 CL Application Note, 1977). For example, a sample applied to a 1.0×25 cm column separated histidine from 3-MH at approximately 213 and 221 min, respectively.

Quantification of Breakdown Products from Body Fluid Samples

To determine the quantity of breakdown products in a sample of body fluid the sample may be treated in the following manner. A urine sample was combined with a known amount of labelled standard, and then combined with an equal volume of 12N HCl and refluxed at 110° C. under nitrogen for 24 h. The hydrolyzed sample was then dried under a stream of nitrogen gas and brought up in 10 ml of 1% acetic acid. The sample was loaded on two disposable columns (Biorad) packed with Sephadex G-15 in 1% acetic acid. The early eluting fractions containing $^{14}C$ radioactivity were collected, reduced to a volume of 1–2 ml with a stream of nitrogen, and loaded on a 2.6×100 cm column (Pharmacia) packed with Sephadex G-15 in 1% acetic acid and run at room temperature. The column had been calibrated with bovine serum albumin and $^3H_2O$ to determine $V_o$ and $V_t$, respectively. Eluted fractions were assessed for absorbance at 280 nm and radioactivity. DES eluted with a $K_{av}$ of about 0.26. The column was flushed with 1% acetic acid until the effluent had no measurable absorbance at 280 nm as compared with 1% acetic acid; usually this required 5 days. The persistence of absorbance indicated the need to replace the contents of the column.

In earlier demonstrations of the method column fractions containing $^{14}C$ radioactivity were pooled; 50% of the pool was analyzed by amino acid analysis as described above and the remainder by HPLC as described below. After these initial studies had validated the HPLC method for quantification of DES and IDES, individual column fractions were run on the HPLC.

The breakdown products were isolated using a modification of the paired-ion $C_{18}$ reversed phase HPLC procedure, generally described in D. Black et al. (1988, Anal. Biochem., Vol. 169, pp. 197–203). A sample of urine was combined with a standard of isotopically labelled breakdown product, for example $^{14}C$-DES. The combined sample was prefractionated in 1% acetic acid as described above and combined with an equal volume of 2×loading buffer (up to 1 ml). Buffers and samples were filtered and degassed before use. Samples and standards in loading buffer were applied on a 1 ml loop into a Varian model 5000 high performance liquid chromatograph equipped with a 0.46×15 cm Vydac C18 column. Solvent A was 20 mM $NH_4Cl$, pH 3.5, containing 5 mM octane sulfonic acid (Aldrich Chemical Co.). Solvent B was 75% acetonitrile:25% Solvent A, with the concentration of octane sulfonic acid adjusted to 5 mM. The loading buffer was 100 mM ammonium acetate/HCl, pH 3.5, containing 50 mM octane sulfonic acid. The column was developed at a flow rate of 1 ml/min as follows. The first 2 min after loading was run at 0% Solvent B; subsequently the proportion of Solvent B was increased by 1% per min to 30%, the concentration was increased to 100% B in the next 10 min and returned to 0% B in the next 8 min. Total cycle time was 52 min. The column effluent was monitored for absorbance at 275 nm using a single channel spectrophotometer, or the absorption spectrum of the effluent from 220–320 nm was recorded using a photodiode array detector, Waters Model 991 controlled by a 991 Software package (version 5.11) run on a NEC Powermate 386 SX+ computer. The amount of HP or LP passing through the detector is quantitated from the absorbance at 295 nm vs time, the amount of DES passing through the detector is quantitated from the absorbance at 268 vs. time, and the amount of IDES passing through the detector is quantitated from the absorbance at 280 vs. time. The area under each peak can be integrated and expressed in absorbance units×min, and the sensitivity of detection for LP, HP, DES, IDES is 0.05 nmoles. Using the software, the ultraviolet spectrum of the purified connective tissue breakdown product is superimposed upon that of a standard and a fit parameter is calculated. A peak purity calculation is also carried out to assess the homogeneity of the material eluting under the shoulders of the peak. In addition a Hitachi model F-1050 with a Model D-2500 Integrator may be used to monitor and integrate the fluorescence of samples of HP or LP. This fluorescence detection is sensitive enough to detect 0.01 nmoles of HP or LP. Thirty second fractions of the effluent were collected for further analysis and quantitation of breakdown products. The quantity of a radioactively labelled purified breakdown product can be determined by liquid scintillation counting, and the amount of breakdown product originally present in the sample can be determined by adjusting for the percentage of the labelled product lost during purification.

Additionally, the quantity of a labelled and endogenous breakdown product can be determined by mass spectrometry or possibly by infrared spectroscopy. The amount of each product will be separately quantitated due to their molecular differences and the decrease in specific activity of added labelled product can be used to determine the amount of endogenous breakdown product originally present in the sample.

Additionally, the amount of breakdown product in a sample can be determined by a radio-immunoassay (RIA) or an enzyme-linked immunosorbent assay (ELISA) after the purification of the sample over the gel filtration columns.

To quantitate the amount of breakdown product in a sample by ELISA, the sample is incubated with an antibody directed against the desired breakdown product. Depending upon a number of factors, such as the amount of breakdown product present, some or all of the product is complexed to the antibody. The antibody is mixed with the purified sample, and then added to a microliter well in which the breakdown product has previously been bound. The remaining uncomplexed antibody will complex with the breakdown product present in the microtitre well. The amount of antibody bound to breakdown product in the well is then measured by the addition of a second antibody that is directed against the first antibody. The second antibody is quantitated by the addition of a substrate which reacts with an enzyme bound to the second antibody, and the enzyme produces and intense color. The color produced is proportional to the amount of second antibody present and the quantity of breakdown product present in the well can be determined using standards of known amounts of breakdown product. The specific activity of the labelled breakdown product after purification is also determined and the amount of breakdown product originally present in the sample is calculated.

To quantitate the amount of breakdown product by RIA, the sample is treated generally as described for an ELISA above. In this case the purified sample is incubated with an antibody, and then a known amount of radio-iodinated breakdown product is added. The antibody that was not complexed to the breakdown product present in the purified sample is complexed to the added radio-iodinated breakdown product. The breakdown product-antibody complexes are precipitated and the amount of radio-iodinated product is determined. The larger the amount of breakdown product present in the original sample, the smaller the amount of radio-iodinated product will be bound and precipitated.

Sample Preparation

The examples following, presented for illustration, demonstrate the use of the invention in an assay for measuring the quantity of connective tissue breakdown products in urine, the described method is also applicable to the measurement of muscle tissue breakdown products.

Samples have been prepared from hamsters and humans. In the initial experimentation, urine was collected for 24 hours and then analyzed for the content of the connective tissue and muscle tissue breakdown products. In the initial experimentation, a portion of the subjects were placed on a meat-free diet prior to the collection of samples. It has been subsequently found that a meat-free diet is not necessary for the quantitation of connective tissue breakdown products. It was also found that a 24 hour urine sample is not necessary to obtain reliable results over time, and that urine samples collected on succeeding days can be normalized to the urinary creatinine concentrations. Urinary creatinine can be measured according to the method described in D. Heinegard et al. (1973, *Clin. Chim. Acta.*, Vol. 43, p. 305).

Analysis of Hamster Urine Samples

Preparation of samples is illustrated by the following examples using hamsters fed standard chow and using hamsters fed a meat-free modified diet. The results are shown in Table 1, showing a comparison of HPLC and AAA 24 h DES and IDES excretion values per hamster.

Before analysis the urine was centrifuged at 30,000× g for 15 min to remove food material and other particulates. Six hamster-days of urine were pooled, usually 15-30 ml, aliquots were removed for determination of creatinine by the method described in D. Heinegard et al. (1973, *Clin. Chim. Acta.*, Vol. 43, p. 305), using a kit (Sigma Diagnostics); a known amount of $^{14}$C-DES (around 500 cpm) was added as a standard, and the aliquot was stored at $-20°$ C. The purification and quantitation of the breakdown products in the sample was determined as described above. G-15 fractions from an individual determination were pooled. One-half of each pool was assessed by amino acid analysis and the other half by HPLC. A ratio of the two values was calculated and found not to be different from 1.0, indicating that amino acid analysis and HPLC yielded similar results.

TABLE 1

| Treatment | DES ($\mu$g) AAA | DES ($\mu$g) HPLC | AAA/ HPLC | IDES ($\mu$g) AAA | IDES ($\mu$g) HPLC | AAA/ HPLC |
|---|---|---|---|---|---|---|
| Example #1 | | | | | | |
| Control | 0.080 | 0.073 | 1.09 | 0.105 | 0.076 | 1.38 |
| HNE | | | | | | |
| a. | 0.158 | 0.139 | 1.14 | 0.160 | 0.138 | 1.16 |
| b. | 0.178 | 0.194 | 0.92 | 0.206 | 0.221 | 0.93 |
| Example #2 | | | | | | |
| Control | 0.075 | 0.061 | 1.23 | 0.076 | 0.067 | 1.13 |
| PPE | 0.273 | 0.258 | 1.06 | 0.275 | 0.256 | 1.07 |
| | | | 1.13 ± 0.07 (n = 5) | | | 1.09 ± 0.05 (n = 5) |

In Example #1 hamsters (100 g) were maintained on standard 5001 Purina Rodent Laboratory Chow. Groups of 8 hamsters were anesthetized by inhalation of carbon dioxide and instilled intratracheally with 0.5 ml saline or 0.5 ml saline containing 300 $\mu$g human neutrophil elastase ("HNE") purified as described in P. J. Stone et al. (1987, *In Vitro Cell. Dev. Biol.*, Vol. 23, No. 10). Urine was collected by placing hamsters in metabolic cages for 3 days. Sodium azide was added to each cup before collection was begun. The cups were emptied at least daily and the contents stored at −20° C.

In Example #2 hamsters were maintained on Purina Modified Lab Chow, in which fish meal, meat meal, bleachable fancy tallow and dried whey were removed from standard rodent chow. To balance the latter formula with fat and protein, corn oil and RP101 soy protein isolate were added and the levels of ground corn and soybean meal were increased. Groups of 6 hamsters were instilled with 0.5 ml saline containing 300 µg HNE or 300 µg porcine pancreatic elastase ("PPE") purified as described in Stone et al. (1987). Collection of urine was initiated immediately after treatment.

For comparison, 2 control groups of 9 hamsters each, one group maintained on modified chow and one maintained on regular chow, were not instilled.

At the end of the 3 day collection period hamsters were anesthetized and studied by lavaging the lungs three times with heparin saline to remove exudate, injecting the lungs with 5 ml of fixative (4CF1G), excising and degassing lungs and measuring lung volume displacement. Three transverse sections were cut from the left lung and paraffin embedded histologic sections were stained with hematoxylin and eosin and were assessed for air space enlargement by measuring the mean linear intercept (see, P. J. Stone et al., 1990, Am. Rev. Respir. Dis., Vol. 141, pp. 47–52), herein incorporated by reference.

Analysis of Human Urine Samples

For demonstration of the assay for DES in human urine, human urine was collected for 24 h in the presence of 0.02% sodium azide at 2° C. from male volunteers ages 34–50 who had never smoked. Volunteers were asked not to eat red meat for 1 day before and during the urine collection. An aliquot of the urine was removed for measurement of creatinine. Other aliquots representing 10% by volume of the 24 h pool were stored at −20° C. after the addition of a known amount of $^{14}$C-DES (around 500 cpm). Aliquots representing as little as 7% or as much as 15% of the 24 h pool were also assayed; results were not different. For analysis the sample was reduced in volume to a viscous orange fluid with a rotary evaporator under reduced pressure from a water aspirator. Forty ml of 6N HCl was added to the sample, which was then hydrolyzed and processed as above. More preferably, the sample can be reduced to a convenient small volume (but not to a viscous orange fluid) and then reconstituted using water and HCl to a final volume of 40 ml in 6N HCl.

For assessment of dialyzable DES and IDES, other aliquots of hamster and human urine samples were dialyzed 3 times in 1% acetic acid, followed by addition of 500 cpm $^{14}$C-DES as above, lyophilization and hydrolysis. The hydrolyzed material was processed as above.

Quantification of Nonradioactive DES Added to Urine Samples

Non-radioactive DES (4.2 nmol) was added to 10% by volume of 24 h human urine samples, the samples were combined with 500 cpm $^{14}$C-DES, and the amount of DES added was verified using the method after prefractionation of Sephadex G-15 and measurement using HPLC as described above.

Quantification of DES and IDES Using Isotope Dilution of $^{14}$C-IDES

Human specimens were combined with 500 cpm of $^{14}$C-IDES and processed as described above. Values for DES and IDES in the specimens were calculated as described above and compared with values obtained in equivalent specimens that had been combined with $^{14}$C-DES.

Statistical Analysis

Values are presented in the Tables and Figs. as the mean ±SE. Statistical analyses involving 2 groups were carried out using the t test for unpaired or, where noted, for paired data. Comparisons involving three groups were made using analysis of variance, the Dunnett test for comparison of groups with the control group, or the Bonferroni test for comparison among all the groups. Probability values of $p < 0.05$ were considered significant.

Comparison of IDES and DES Recoveries

Human urine samples were combined with 500 cpm each of $^{14}$C-DES and $^{14}$C-IDES and processed as above. Sephadex G-15 fractions containing radioactivity were combined into pools, early fractions containing the peak fraction and later fractions containing lesser amounts of radioactivity. Each pool was separately loaded on an amino acid analyzer and the radioactivities eluting with DES and IDES were separately assessed and compared.

The following two examples demonstrated that the % recovery of IDES and DES were not different. In a first example 147 cpm of DES and 137 cpm of IDES were recovered from the amino acid analyzer after loading the early fractions; respectively 58 cpm and 64 cpm were recovered from the late fractions or a total of 211 cpm and 195 cpm for DES and IDES, respectively, or recoveries of 42% and 39%. Including the loss of radioactivity owing to formation of $^{14}$CO$_2$(17%) and the 150 cpm used to evaluate the radioactivity of eluted fractions, the overall recovery exceeded 60%. In a second example 153 cpm and 159 cpm of DES and IDES were recovered in the early fractions and 34 cpm and 28 cpm in the later fractions. Similar relative recoveries of DES and IDES in the early and late fractions suggested that DES and IDES co-eluted from the G-15 column; if they had not co-eluted the early fractions would be relatively enriched in either DES or IDES. Combining the urine samples with both $^{14}$C-DES and $^{14}$C-IDES appeared to improve the recovery of radioactivity as compared with combining the sample with either DES or IDES alone, suggesting that losses were not simply proportional to the amounts initially present. Thus, the losses of DES and IDES are not constant or predictable from sample to sample.

Comparison of Results From Amino Acid Analysis and HPLC in Hamsters

Results obtained with hamster samples that were analyzed by amino acid analysis ("AAA") and HPLC were compared as follows. One-half of the pool was assessed by AAA and the other half by HPLC (Table 1). A ratio was determined by dividing the DES or IDES AAA value by the corresponding HPLC value for each of 5 samples, although AAA values tended to be larger than HPLC values. The mean value for the 5 ratios was not different from 1.0 indicating that the values obtained by AAA and HPLC were not different from each other.

Values for Hamster Samples

Representative urinary DES and IDES values per hamster per day for 3 treatments: control (untreated), HNE or PPE, are presented in Table 2, which shows DES and IDES excretion values for hamsters in Example 2 of Table 1.

TABLE 2

| Treatment | DES (μg) | IDES (μg) | MLI (μm) |
|---|---|---|---|
| none | 0.074 ± 0.008 (8) | 0.087 ± 0.005 (8) | 54 ± 2 (9) |
| HNE | 0.212 ± 0.012 (2) | 0.245 ± 0.019 (2) | 64 ± 2 (6) |
| PPE | 0.816 ± 0.005 (2) | 0.826 ± 0.072 (2) | 86 ± 5 (6) |

Urine for each treatment group was collected for 3 days after treatment, pooled and analyzed for DES and IDES. The lungs were fixed and the left lung was used to determine the mean linear intercept. Values are given as the mean ±SE (no. of determinations). Twenty-four hour creatinine values per hamster were 2.19±0.15(5), 1.61±0.07(2) and 0.84±0.03(2) mg, respectively, for untreated, HNE-treated and PPE-treated. No differences were found between untreated hamsters on meat-free chow and regular chow; data from those two groups were combined.

With doses of HNE and PPE representing dearly equimolar amounts, the DES levels in the urine were respectively 3 and 11 times those found in urine of untreated hamsters. If all of the increase in DES excretion were from the lungs, this would represent 74 and 400 μg of lung elastin, respectively, based upon 3000 μg of elastin in the lungs with an elastin amino acid composition of 0.9 residues DES per 1000 residues amino acids (see, Starcher et al., 1977). After the 3 day urine collection HNE and PPE had produced airspace enlargements of 119% and 159% of control, respectively. Dialysis of urine from untreated or HNE-treated hamsters using dialysis tubing with a 1000 dalton cutoff removed more than 85% of the DES and IDES. With PPE treatment, use of tubing with a 2000 dalton cutoff removed 70%; a significant amount of DES and IDES peptides with molecular mass greater than approximately 2000 daltons was apparently present. There was no difference between the urinary DES values for hamsters on the regular chow and those on meat-free chow; the groups were combined for data presentation. Twenty-four h urine creatinine content of HNE- and PPE-treated hamsters was significantly decreased as compared with the untreated group as were the volumes (2.85 ml for HNE-treated, 2.0 ml for PPE-treated and 5 ml per day for untreated hamsters).

Values for Human Specimens 24 hour urine specimens were collected from eight normal male volunteers who were never smokers. The specimens were analyzed for DES and IDES concentration using the method of the invention, and an aliquot of the specimen was removed for measurement of creatinine using a kit (Sigma Diagnostics, St. Louis, Mo.). Three 24 h specimens obtained from volunteer #1 over a 4 month period were analyzed by AAA, AAA and HPLC, or HPLC only, respectively. There were no differences among the specimens. The 24 hr values [mean±SEM (n)] were 8.3±0.1(2) μg DES and 8.2±0.1(2) μg IDES for the first specimen (analyzed by AAA), 8.6±0.9(5) μg DES and 7.5±1.0(5) μg IDES for the second specimen (analyzed by both AAA and HPLC), 6.5±1.4(3) μg DES and 7.1±0.5(3) μg IDES for the third specimen (analyzed by HPLC): For volunteer #2 two specimens collected 3 months apart had 24 h DES values of 8.9±0.8 μg (6) and 8.2±0.7 μg (6). Single samples were taken from the other 6 volunteers, and the values, expressed μg DES or IDES/g creatinine are shown in Table 3 along with 24 h creatinine values and the number of replicate determinations (n).

TABLE 3

| Volunteer # (g creatinine/day) | DES (μg/g) | IDES (μg/g) | (n) |
|---|---|---|---|
| #1 (1.6 g) | 4.9 ± 0.4 | 4.9 ± 0.3 | (n = 10) |
| #2 (1.7 g) | 6.1 ± 0.3 | 5.0 ± 0.3 | (n = 13) |
| #3 (2.0 g) | 5.6 ± 0.3 | 4.5 ± 0.2 | (n = 8) |
| #4 (2.0 g) | 4.9 ± 0.6 | 4.2 ± 0.4 | (n = 7) |
| #5 (1.8 g) | 7.3 ± 0.4 | 5.5 ± 0.4 | (n = 9) |
| #6 (2.8 g) | 8.3 ± 0.8 | 7.8 ± 0.6 | (n = 7) |
| #7 (2.1 g) | 9.4 ± 0.7 | 6.6 ± 0.6 | (n = 10) |
| #8 (1.8 g) | 5.3 ± 0.5 | 5.6 ± 0.2 | (n = 5) |

There appeared to be a linear relationship between urinary creatinine and DES and urinary creatinine and IDES values, with a mean value in this study of 6.5±0.7 μg DES/g creatinine, and 5.5±0.4 μg IDES/g creatinine.

Dialysis of human urine using tubing with a 1000 dalton cutoff decreased the DES and IDES values by more than 85%. Recovery of a bolus of unlabelled DES (4.2 nmol) that had been added to a urine sample was assessed by HPLC. Excluding the DES added as $^{14}$C-DES, 6.2±0.5 (4) nmol was present in the urine sample, representing 10% by volume of the 24 h pool from volunteer #2. After subtraction of the endogenous DES determined in earlier experiments (1.7 nmol) we calculated that 4.5±0.5 nmol DES (n=4) had been added, a value that was not significantly different from 4.2 nmol DES that was, in fact, added.

The variability of values obtained for a specimen using 4 sequential eluted fractions from the large G-15 column was determined by HPLC, and the results are presented in Table 4. The standard error for the calculated DES and IDES values was 5 and 8% of the mean, respectively.

TABLE 4

| Fraction # | $^{14}$C-DES recovered (CPM) | nmol in DES | fraction IDES | μg/24 h DES | calculated IDES |
|---|---|---|---|---|---|
| 58 | 20 | 0.0878 | 0.0829 | 9.4 | 12.6 |
| 59 | 43 | 0.1844 | 0.1422 | 9.1 | 10.1 |
| 60 | 46 | 0.1866 | 0.1313 | 8.4 | 8.7 |
| 61 | 34 | 0.1624 | 0.1064 | 10.6 | 9.5 |

The radioactivity present in the DES eluting from the HPLC was determined. Recovery in the 4 fractions of the radioactivity initially present (579 cpm) was 25% Including the 56 cpm lost in determining which G-15 fractions contained $^{14}$C-DES, recovery was 34%. A representative calculation of the nmol DES and IDES present in fraction #60 is described below with respect to FIG. 2. Calculation of 24 h values based upon the results of fraction #60 are as follows. The specific radioactivity of DES in fraction #60 is 247 cpm/nmol as compared with 776 cpm/nmol for the $^{14}$C-DES combined with the sample, 3.14×0.746 nmol was present in the sample after the labelled DES was added or 1.60 nmol of endogenous DES (after subtraction of the 0.746 nmol representing the added DES). The sample represents 10% by volume of the 24 h pool. The molecular mass used for DES is 526 daltons, so that 1.60 nmol×526 ng/nmol×10=8.4 μg DES present in the 24 h urine. The calculation for IDES is based upon our finding of similar recoveries for DES and IDES, i.e., 46 cpm in this fraction out of the original 579 cpm added.

The method gave similar results whether we used $^{14}$C-DES or $^{14}$C-IDES; calculated values for DES and IDES in specimens combined with $^{14}$C-IDES were not different from the values obtained in equivalent specimens that had been combined with $^{14}$C-DES.

FIG. 1 shows a representative chromatogram of a hydrolyzed human urine sample combined with $^{14}$C-DES (579 cpm) after loading on a 2.6×100 cm column packed with Sephadex G-15 and run in acetic acid. The sample had been prefractionated on a 20 ml disposable column packed with Sephadex G-15. With a flow rate of 0.23 ml per min, 3.5 ml fractions were collected, assessed for absorbance at 280 nm (solid line) and 0.35 ml assessed for $^{14}$C radioactivity (dashed line); data points for fraction numbers 58–61 are indicated by reference numerals 58–61 in FIG. 1. After subtracting background the radioactivity values were multiplied by 10, because 10% of the 24 h urine was the aliquot taken for analysis, and by the quench correlation factor (1.05). The data for fractions ##58–61 are given in Table 4, and the HPLC chromatogram for fraction #60 (210 ml) is shown in FIG. 2.

Overall the two gel exclusion steps removed more than 99.9% of the 280 mn absorbing material, while $^{14}$C-radioactivity losses were approximately 40%. Without both chromatographic steps, material loaded on the amino acid analyzer or the HPLC produced high background absorbance so that IDES and DES were difficult to quantify. Indeed, the amount of DES and IDES in the last G-15 fraction, and sometimes the last two fractions, containing $^{14}$C-DES or $^{14}$C-IDES radioactivity were difficult to quantify because of nonspecific interference from 275 μm absorbing material.

Figure 2:
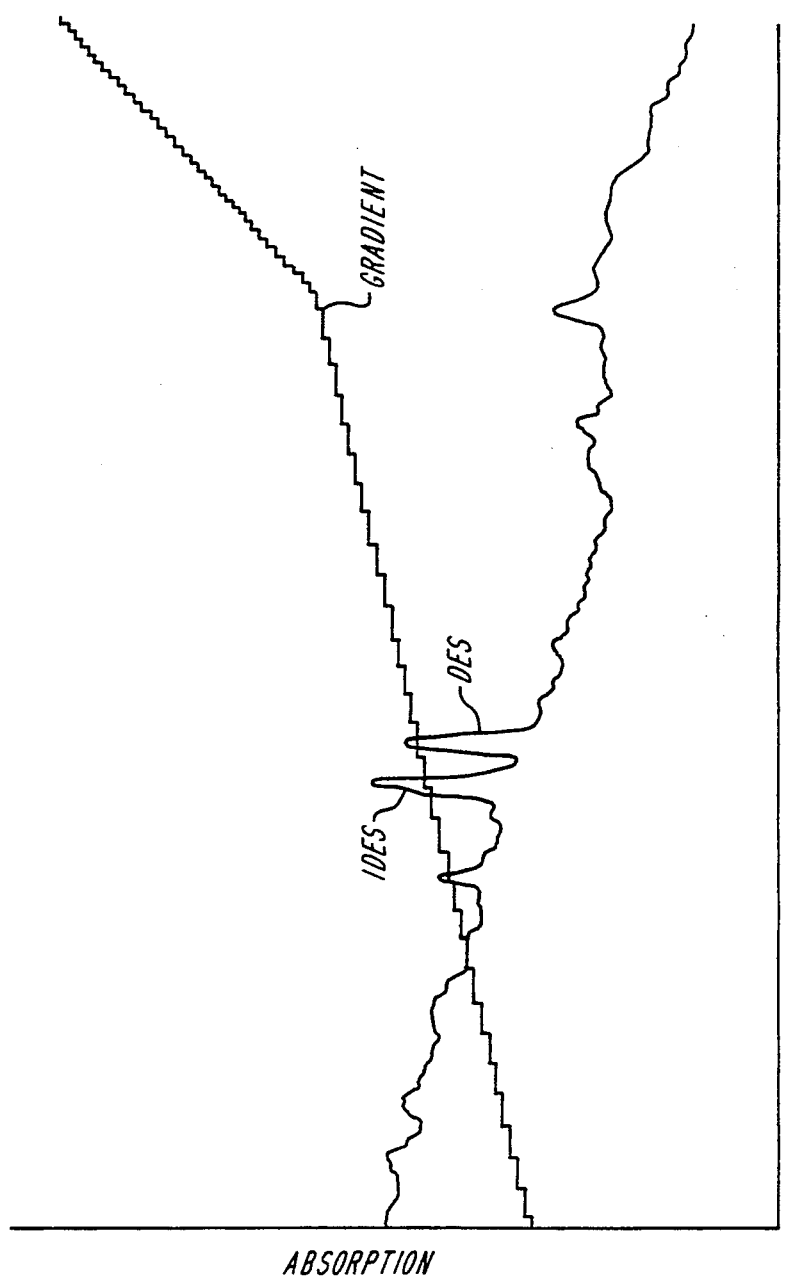
FIG. 2 is a representative HPLC chromatogram for fraction #60 from the sample shown in FIG. 1.

FIG. 2 shows a representative HPLC chromatogram of fraction #60 from the prefractionated sample of hydrolyzed human urine combined with $^{14}$C-DES shown in FIG. 1. The full range of the y axis in FIG. 2 represents 0.05 absorbance units at 275 nm. Comparison with the HPLC peak for $^{14}$C-DES and $^{14}$C-IDES indicates the presence of 0.180 nmol DES in the peak at 23.1% B and 0.131 nmol IDES at 23.8% B. The calculation of the 24 h values is described [above] with reference to Table 4. For fractions #62 and #63 the amount of $^{14}$C-DES recovered was low and the level of background absorbance interfered with accurate determination of the DES and the IDES peak heights.

Figure 3:
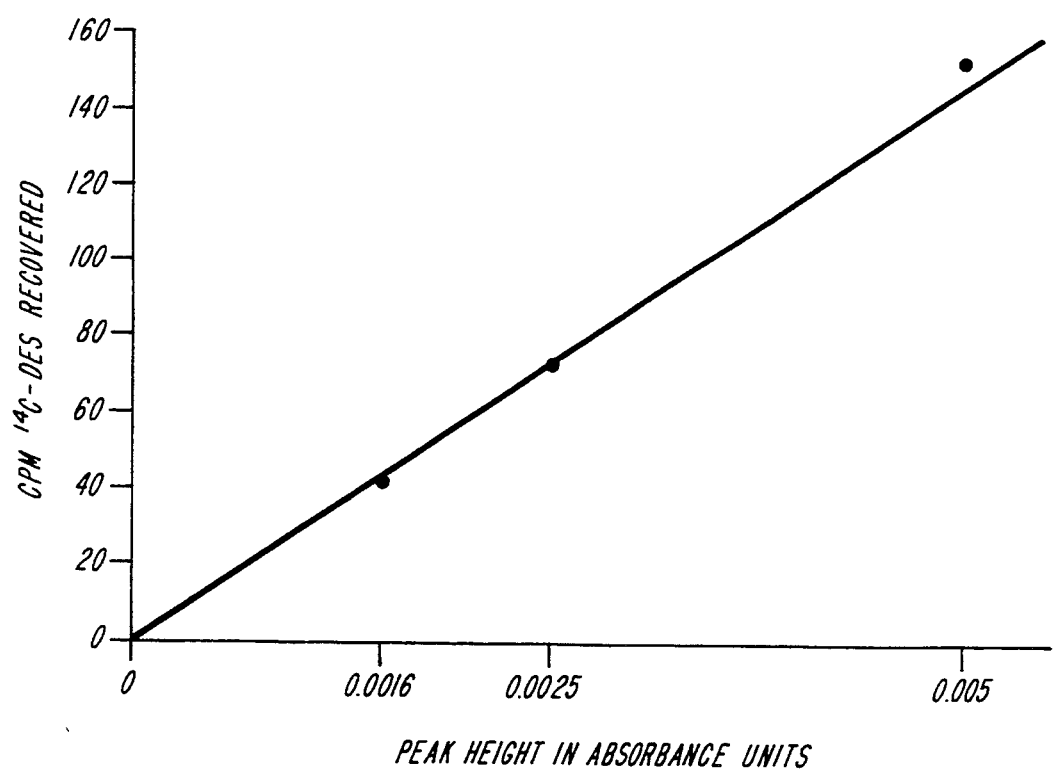
FIG. 3 is a calibration curve for $^{14}$C-DES recovered as a function of peak height on an HPLC chromatogram as in FIG. 2.

FIG. 3 shows a calibration curve for $^{14}$C-DES (cpm) recovered as a function of peak height on the HPLC. Background cpm have been subtracted. The correlation coefficient for the linear regression line shown is r greater than 0.999. As FIG. 3 shows, there was a linear relationship between $^{14}$C-DES radioactivity recovered and the maximum absorbance of the DES peak when $^{14}$C-DES standards were run on the HPLC. Separation of IDES and DES in the chromatogram is 0.6 min. Using AAA well resolved peaks, 4 min apart, were obtained for IDES and DES.

Analysis of Disease Processes in Humans

The method was used to analyze disease processes in humans as will be described below. During the analyses it was found that the natural biological form of the collagen tissue breakdown products is free crosslinking amino acids, which do not require acid hydrolysis for detection. The breakdown products from pathological processes that degrade collagen are found in peptide form in the fluid samples and thus the sample must be acid hydrolyzed in order to accurately quantitate these crosslinking amino acids. This difference in the forms of collagen breakdown products resulting from the natural and pathologic processes can be used to establish a baseline for an individual of the amount of breakdown products normally present in body fluids. The natural biological form of breakdown products of elastin and muscle tissue may also be in the free form and perhaps may also be used to establish a baseline for an individual, as has been shown for collagen.

When monitoring disease processes that resulted in the breakdown of more than one of the elastin, collagen, or muscle breakdown products, it was found to be important to combine the body fluid sample with a labelled standard for each breakdown product that one wished to measure. As discussed above for DES and IDES, the recovery of each breakdown product is not constant or predictable, and the measurement of each desired breakdown product using its labelled standard is preferred.

Figure 4B:
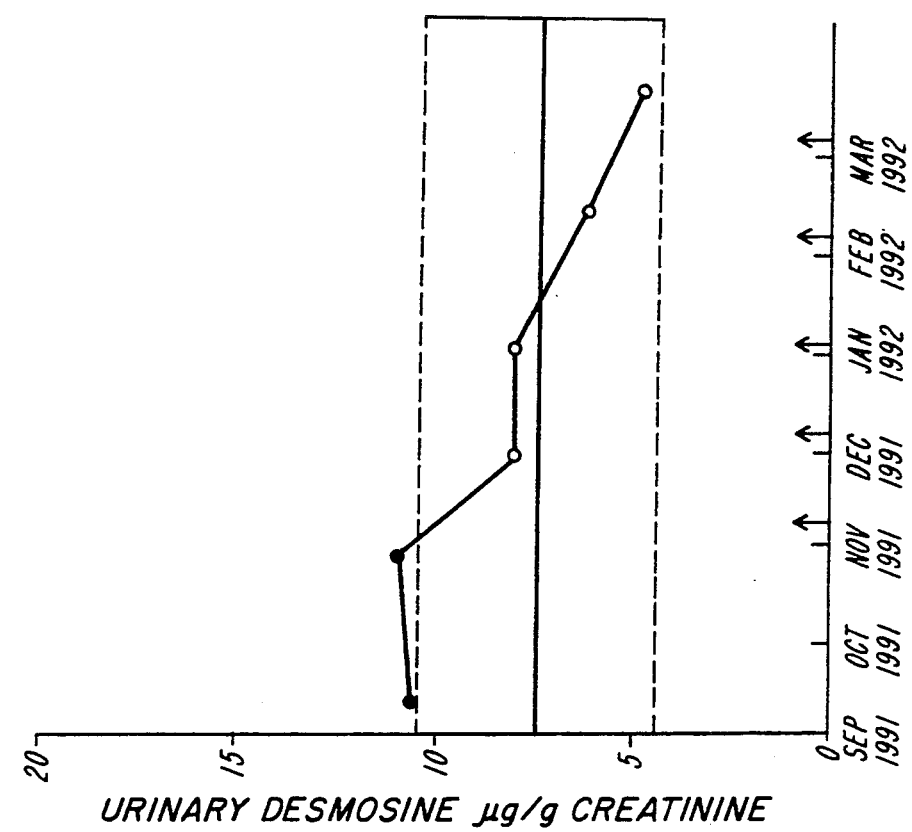
FIGS. 4A and 4B are graphs of urinary desmosine ("DES") levels in two separate individuals who suffer from a genetic deficiency of alpha-1-antitrypsin both before and during treatment with an infusion of alpha-1-antitrypsin. The quantities of these breakdown products have been normalized using urinary creatinine concentration.
Figure 4A:
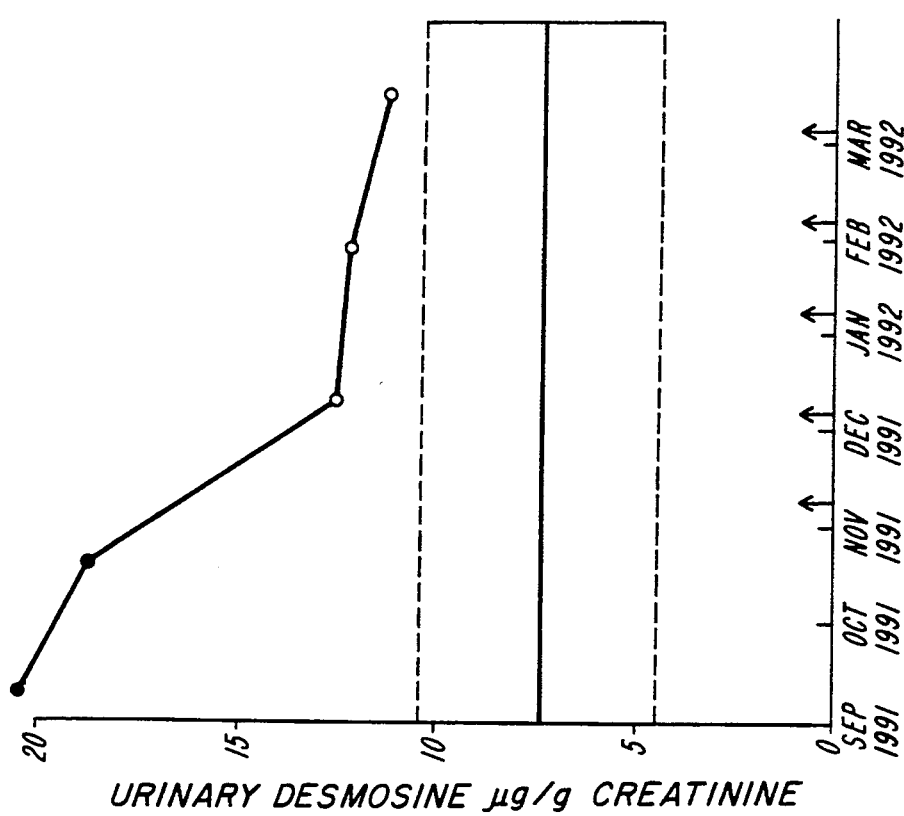

The method was used to analyze disease processes in humans having lung emphysema due to a genetic deficiency of alpha-1-antitrypsin. This disease is characterized by high levels of elastin breakdown products, but not collagen breakdown products in a body fluid sample. This deficiency has been treated experimentally by replacement therapy for almost 10 years, but the efficacy of this treatment has not yet been determined; the invention provides for assessment of such therapies as is demonstrated below. With reference now to FIGS. 4A and 4B, the urinary desmosine concentration of two patients having a genetic deficiency of alpha-1-antitrypsin was monitored over a period of several months, and the quantity of desmosine determined at each time point was normalized using the quantity of urinary creatinine, as is well known in the art. The normal range of DES in μg/g creatinine is shown in the shaded bar extending across each FIG. 4A and 4B. The patients were each treated with an infusion of alpha-1-antitrypsin at the points marked with the bold arrows. As is apparent from the Figs., the patients response to treatment was reflected in the decrease in amount of DES found in the urine. Thus the method of the invention can be used to verify the efficacy of a therapy for a disease process.

Figure 5A:
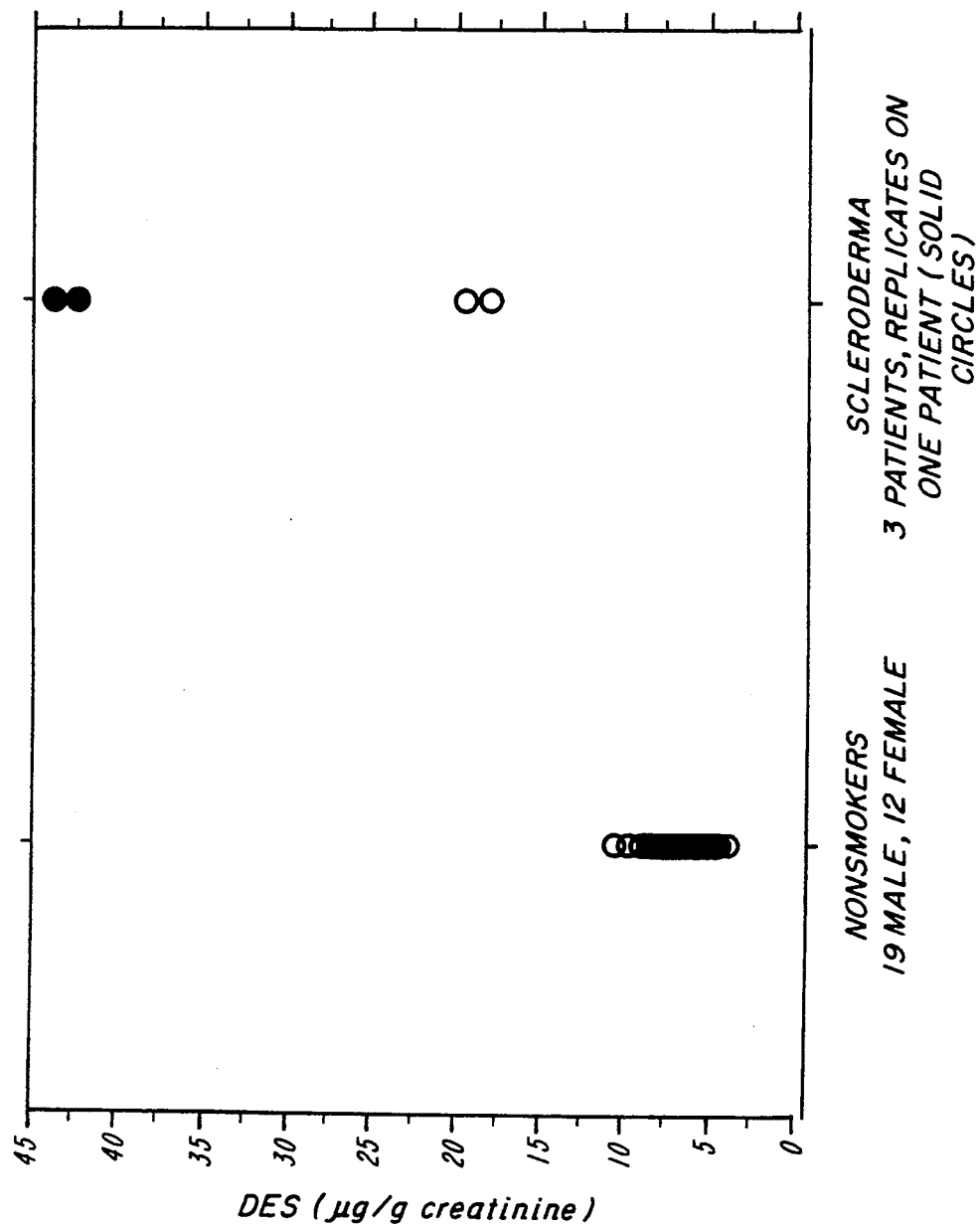

The method was also used to analyze the amounts of DES and HP in the urine due to the disease scleroderma. Scleroderma is a disease about which very little is known. It is manifest by the appearance of fibrotic, scar-like, connective tissue on the skin and in the organs, which eventually results in death. With reference now to FIGS. 5A and 5B, the values of DES in μg/g creatinine and HP in nmol/mmol creatinine are shown, respectively. The values for DES and HP are elevated in the urine of individuals having scleroderma as compared to the control individuals, who are a group of nonsmokers. Note that one patient, solid circles, has greatly elevated DES and HP levels in two replicates. This elevation corresponds with the clinical diagnosis that this patient had diffuse cutaneous ("aggressive") scleroderma. As patients suffering from scleroderma are treated with new therapies, the efficacy of such therapies can be monitored using the method of the invention.

Figure 6:
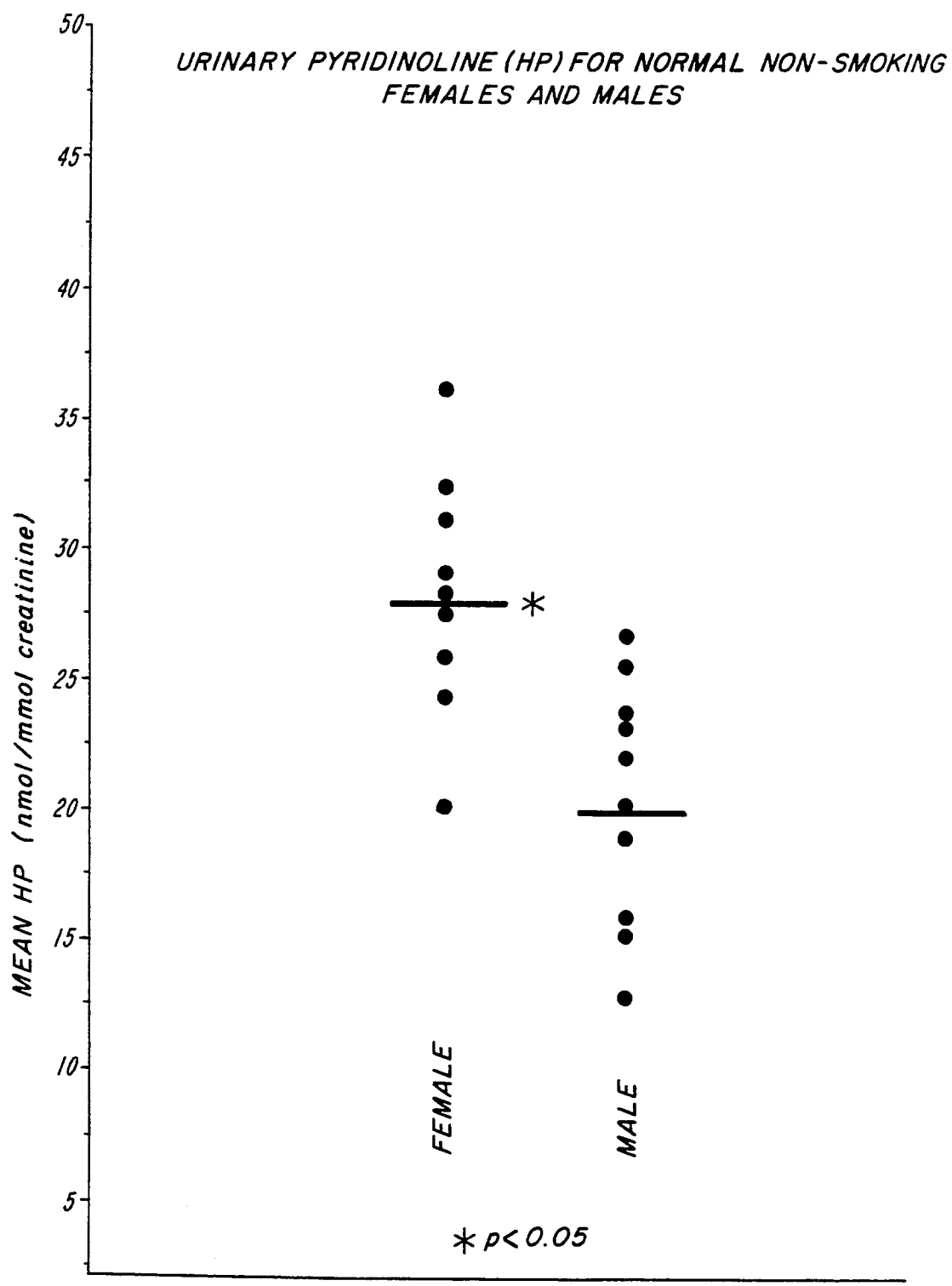
FIG. 6 is a graph of the urinary HP concentration for males and female, normalized using urinary creatinine concentration.
Figure 7A:
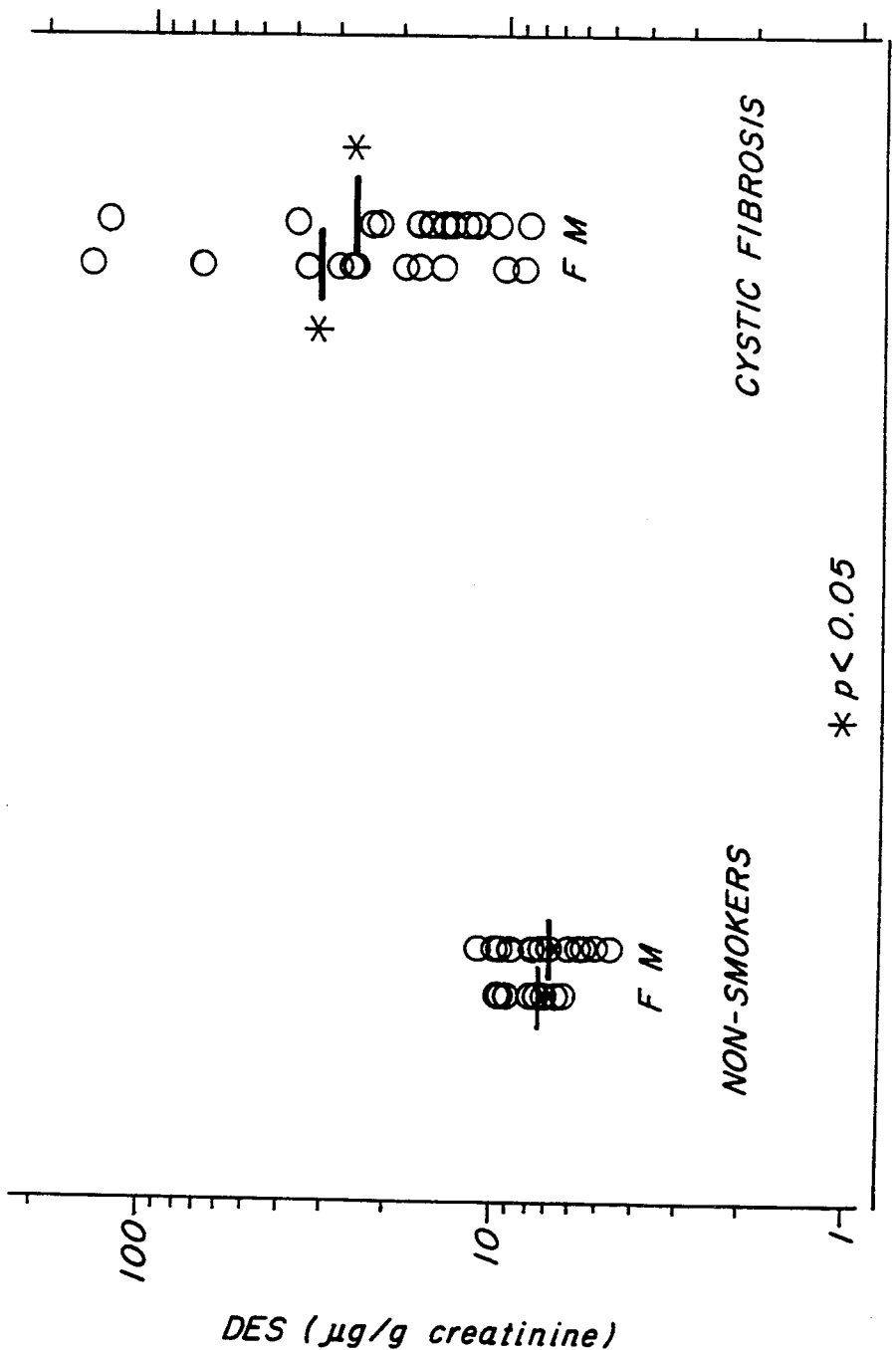
FIGS. 7A and 7B are graphs of the urinary DES and HP concentrations, respectively, normalized using urinary creatinine concentration, for male and female non-smokers and male and females suffering from cystic fibrosis.
Figure 7B:
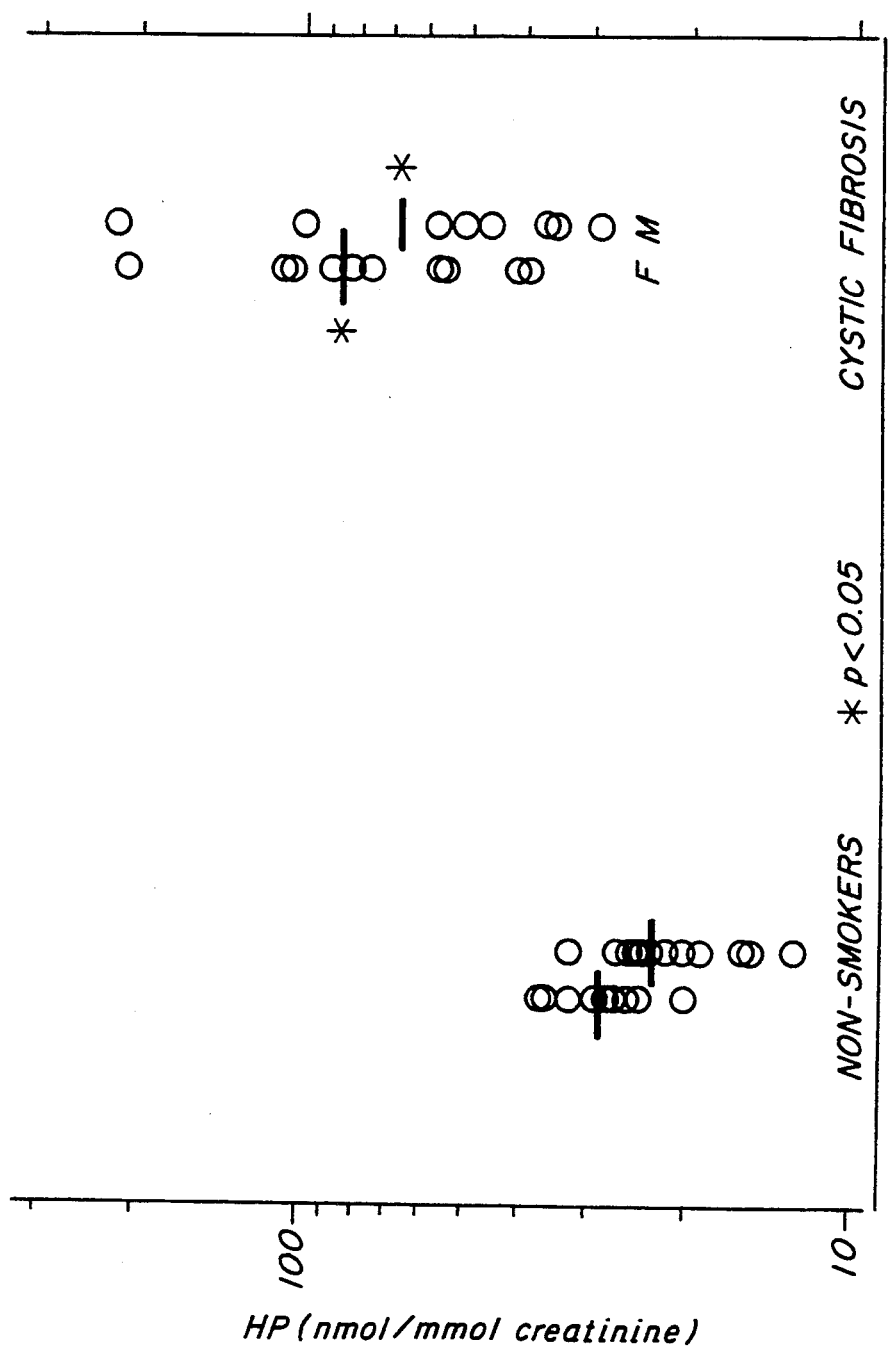
Figure 8:
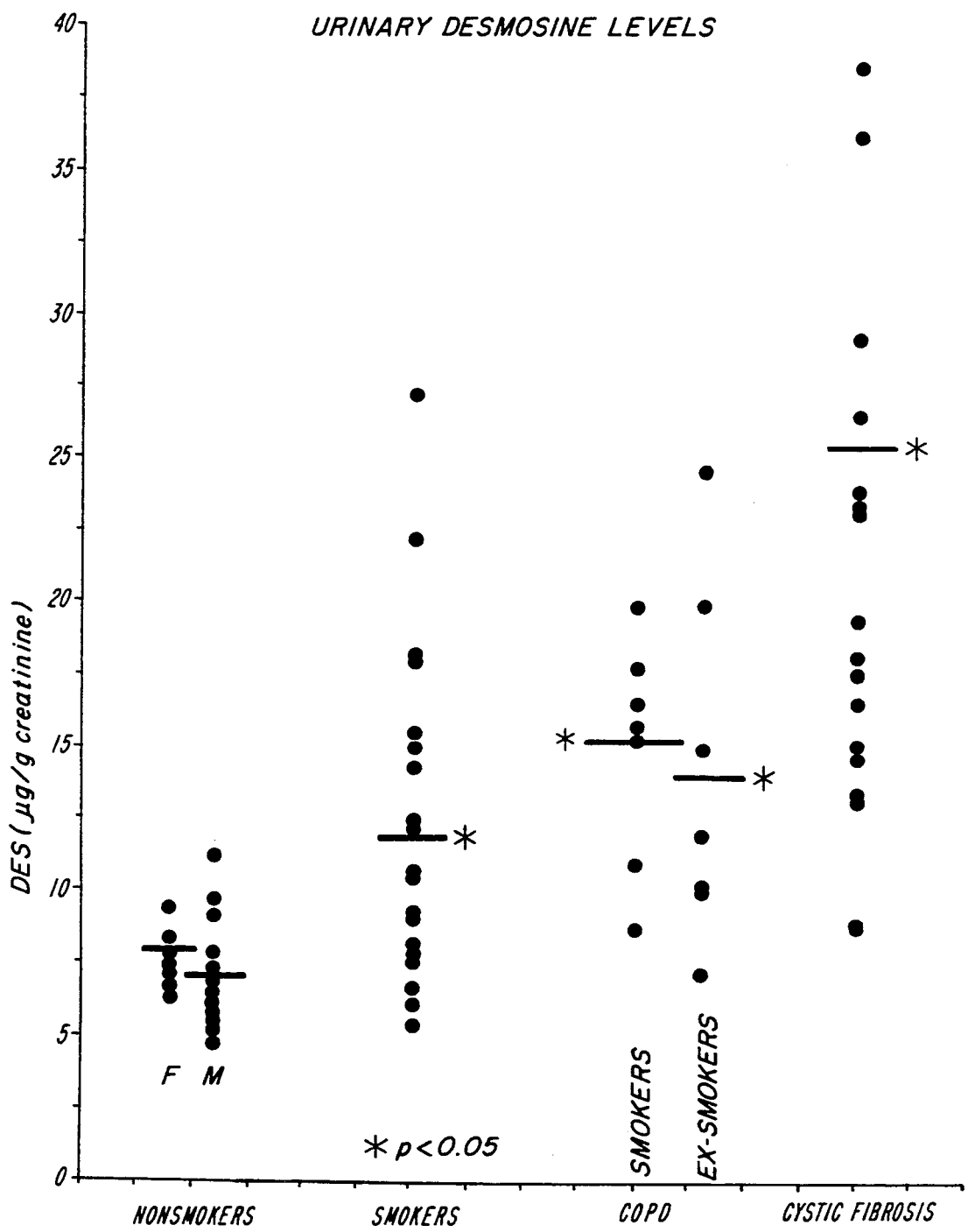
FIG. 8 is a graph of urinary desmosine levels, normalized using urinary creatinine concentration, for male and female non-smokers, smokers, patients with chronic obstructive pulmonary disease "COPD" (both for smokers and ex-smokers), and for patients with cystic fibrosis.

The method was also used to quantitate the amounts of DES and HP in normal individuals who are non-smokers and in individuals who are suffering from cystic fibrosis or chronic obstructive pulmonary disease "COPD". With reference now to FIG. 6, data showing the amount of HP in normal non-smoking males and females is shown. The mean value of HP is denoted by a horizontal bar; note that females have a statistically higher quantity of HP in the urine than males. This elevation may be due, in part, to the degradation of mature collagen in the uterus. FIGS. 7A and 7B compare the concentration of DES and HP, respectively, in the urine of normal non-smoking individuals with those suffering from cystic fibrosis, note the log scale. The horizontal bar denotes the mean of the values shown. The individuals with cystic fibrosis show more than a 3-fold increase in the urinary levels of DES and HP than normal individuals. FIG. 8 shows a comparison of normal non-smokers (both male and female), smokers, patients having COPD (both smokers and ex-smokers), and patients with cystic fibrosis. The horizontal bar indicates the mean of the values presented.

In addition to monitoring the disease processes described above, the method may also be useful for monitoring the disease process of autoimmune connective tissue diseases such as systemic lupus erythematosus.

Monitoring of Normal and Abnormal Processes in Humans.

Figure 9A:
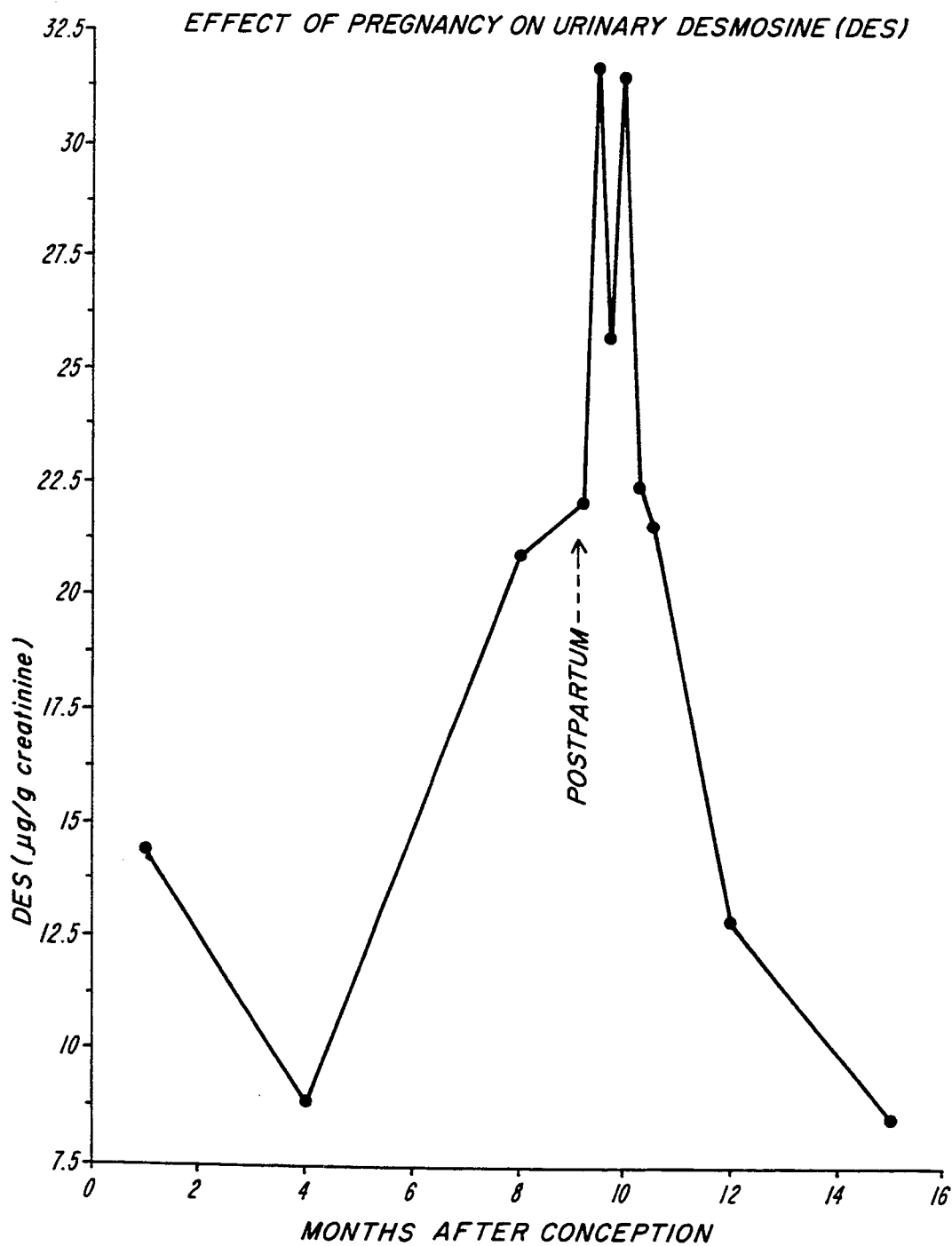
FIGS. 9A and 9B are graphs of the urinary desmosine and pyridinoline concentrations, normalized using urinary creatinine concentration, at succeeding months after conception and postpartum, respectively.
Figure 9B:
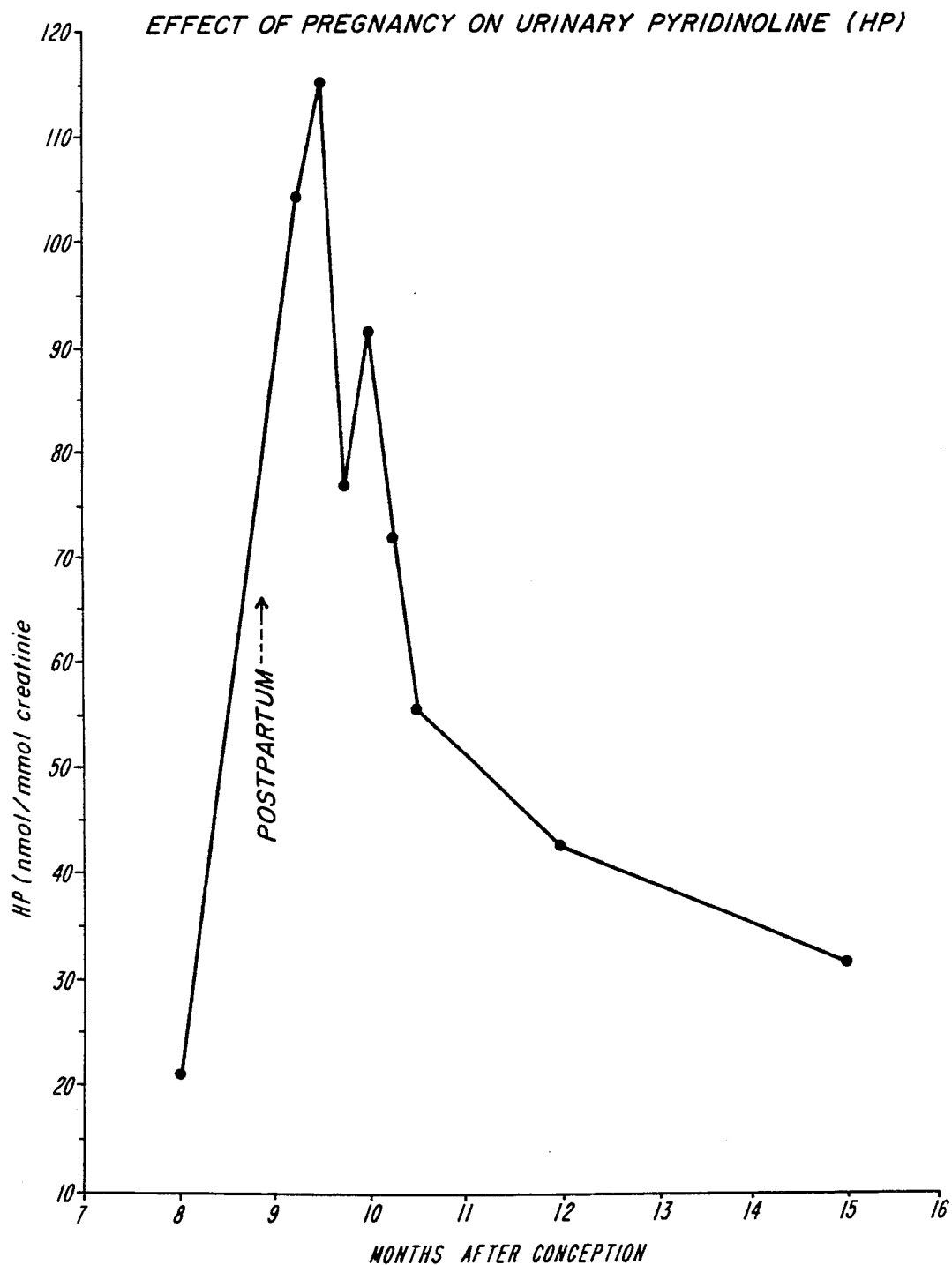

The method was used to monitor pregnancy, and the involution of the uterus in the postpartum period. With reference now to FIGS. 9A and 9B, urinary DES and HP levels, respectively, were determined after conception, and in the postpartum period. The amounts of DES and HP were normalized to creatinine as is well known in the art. Note that the concentration of DES is greatly elevated prior to the postpartum period, and that the concentration of both DES and HP increase greatly in the early postpartum period. The elevation of DES during pregnancy may reflect DES from the fetus, and may be a normal indication. The elevation of DES and HP during postpartum may be a result of the involution of the uterus with the attendant degradation of connective tissue as the uterus returns to its normal size. A large increase in the values of DES and HP during the term of pregnancy may indicate an impending miscarriage.

Use

The method of the invention can be used for assessment of a disease process that includes connective tissue breakdown, and/or muscle tissue breakdown, by providing accurate quantitative determination in a body fluid of a specific breakdown product of the connective or muscle tissue.

The monitoring of a plurality of connective tissue and muscle tissue breakdown products can provide a diagnostic measure of a pathologic condition. For example, if sepsis were present in the lung, breakdown of collagen and elastin would be elevated and high values of DES, IDES, HP, and LP would be found in a body fluid sample. In addition, a high level of 3-MH would be found in the body fluid sample, thus identifying the disease as sepsis of the lung. If sepsis were present in a different tissue that was deficient in elastin, but contained collagen, such as bone, the values of 3-MH, HP, and LP would be elevated in a body fluid sample, but the values of DES and IDES would most likely be normal.

Urinary DES (and IDES) values did not differ for normal individuals by more than 10% when measured according to the invention on different occasions. Calculated values for endogenous DES and IDES in aliquots that had been combined with $^{14}$C-IDES were not different from values determined using equivalent aliquots that had been combined with $^{14}$C-DES. Values for DES and IDES in the urine were rarely more than 20% apart, reflecting the known relative DES and IDES composition of human and hamster elastin.

Because the method yields results consistent over time, it can be used to assess or monitor the efficacy of a therapeutic for a disease condition that includes connective tissue breakdown by, for example, comparing a connective tissue breakdown product measurement made prior to instituting the therapy with one or measurements made during the course of or following the therapy. Such an assessment can be particularly useful where a variety of therapies are available, and where there is substantial variation in patients responses to a particular therapy, for selection of the most efficacious therapy in a relatively short time by trial-and-error.

The assay for elastin and collagen breakdown products can be used to determine a person's history of smoking tobacco, particularly for actuarial purposes. Preliminary results suggest that urinary connective tissue breakdown products may be substantially elevated in persons who smoke tobacco as compared with persons who have never smoked; and that urinary connective tissue breakdown products may be elevated to a lesser degree in persons who have a prior history of smoking but who no longer smoke.

The values for DES in human and hamster urine, as determined according to the invention, are smaller by a factor of 5–10 than values reported using methods employing RIA. One explanation for this difference is that urine may contain components that can erroneously elevate values that have been determined using an antibody. Antibody preparations directed against DES can cross-react towards the collagen crosslink, pyridinoline, which is present in higher concentrations in human urine than DES; and non-specific interferences can occur in ELISA methods for determining urinary DES. Thus, for example, if as much as 90% of previously reported DES values were impurities, a doubling of DES output would have increased the measured value by only 10–20%, an amount well within the standard error of the method.

The method of urinary DES measurement according to the invention can be useful for understanding diseases such as chronic obstructive pulmonary disease ("COPD") and cystic fibrosis ("CF"), where the elastase and neutrophil load of the lungs is increased, and elastin and collagen destruction in the lungs is believed to be an ongoing part of the disease process. A decrease in an elevated level of urinary DES associated with COPD or CF following treatment with a supplemental antielastase would be indirect evidence that the disease process had been interrupted. The early diagnosis and therapy of other conditions, such as acute respiratory distress syndrome and metastatic tumors of the lung, where a protease imbalance is thought to be present in the proximity of connective tissues, can be facilitated by measurement of urinary connective tissue breakdown products.

Other Embodiments

Other methods than gel permeation chromatography may be used for the removal step. However, because connective tissue cross-linking amino acids are so large in comparison to other amino acids, and because the hydrolysis step yields substantially a mixture of amino acids and other small molecules, prefractionation according to molecular size is preferred. Using Sephadex G-15, the large crosslinking amino acids elute very early and cleanly.

Labelled breakdown product can be provided by means other than production in culture; for example, breakdown products can be labelled by tritium exchange or by some other chemical method. Preferably, the label does not alter those properties of the product in such a way that the behavior of the labelled product in the prefractionation or separation steps is rendered substantially different from that of the unlabelled product.

Other disease processes which cause the degradation of connective tissue or muscle tissue may be monitored using the method describe herein. For example, atherosclerosis may cause excess degradation of elastin and/or collagen in large blood vessels afflicted with atherosclerotic lesions. The measurement of breakdown products in a body fluid may provide an indication of the severity of these lesions. Additionally, cancerous tumors are known to secrete proteases which digest the surrounding connective tissue, thus allowing the spread of cancerous cells, the spreading of which may be reflected in the presence of high concentrations of connective tissue crosslinks in the patients body fluids. Thus we believe the measurement of breakdown products in a body fluid may yield insights into the progression of various diseases and aid in the choice of therapeutic procedures to be utilized.

We claim:

1. A method for quantitatively determining the amount of a tissue breakdown product from at least one of a connective tissue or a muscle tissue, in a body fluid from an animal, comprising
   providing a standard comprising a breakdown product having an isotopic label, said label being radioactive or non-radioactive,
   combining a known quantity of said standard, containing a known quantity of said label, with a sample of the body fluid,
   substantially purifying from said combined standard and sample a breakdown product fraction containing labelled breakdown product from said standard together with breakdown product from the sample, and
   measuring the quantity of breakdown product and the quantity of label in the substantially purified breakdown product fraction, whereby the measured recovery of the label in the substantially purified breakdown product fraction and the quantity of label in the original standard which was combined with the sample provides a measure of the proportionate loss of breakdown product during the purifying step.

2. The method of claim 1 further comprising normalizing the quantity of measured substantially purified breakdown product to the quantity of creatinine present in the body fluid sample.

3. The method of claim 1 wherein said substantially purifying step comprises treating said combined standard and sample by chromatography.

4. The method of claim 3 wherein said substantially purifying step comprises treating said combined standard and sample by gel permeation column chromatography.

5. The method of claim 4 wherein said substantially purifying step comprises treating said combined standard and sample by gel permeation column chromatography with a dextran gel having an exclusion volume corresponding to approximately 1,500 daltons.

6. The method of claim 1 wherein said measuring step comprises using high performance liquid chromatography to measure the quantity in said substantially purified breakdown product fraction of said isotopically labelled breakdown product together with breakdown product from the sample.

7. The method of claim 1 wherein said measuring step comprises using amino acid analysis to measure the quantity in said substantially purified breakdown product fraction of said isotopically labelled breakdown product together with breakdown product from the sample.

8. The method of claim 1 wherein said measuring step comprises using liquid scintillation counting to measure the quantity of label in said substantially purified breakdown product fraction of said isotopically labelled breakdown product from said standard together with breakdown product from the sample.

9. The method of claim 1 wherein said measuring step comprises using mass spectrometry to separately quantitate the amount of purified breakdown product and the amount of said purified isotopically labelled breakdown product.

10. The method of claim 1 wherein said measuring step comprises using infrared absorption spectroscopy to separately quantitate the amount of purified breakdown product and the amount of said purified isotopically labelled breakdown product.

11. The method of claim 1 wherein said measuring step comprises using a radioimmunoassay to measure the quantity in said substantially purified breakdown product fraction of said isotopically labelled breakdown product together with breakdown product from the sample, 12. The method of claim 1 wherein said measuring step comprises using an enzyme-linked immunosorbent assay to measure the quantity in said substantially purified breakdown product fraction of said isotopically labelled breakdown product together with breakdown product from the sample.

13. The method of claim 1 wherein the connective tissue breakdown product is desmosine, and said labelled breakdown product is labelled desmosine.

14. The method of claim 1 wherein the connective tissue breakdown product is isodesmosine and said labelled breakdown product is labelled isodesmosine.

15. The method of claim 1 wherein the connective tissue breakdown product is pyridinoline, and said labelled breakdown product is labelled pyridinoline.

16. The method of claim 1 wherein the connective tissue breakdown product is deoxypyridinoline, and said labelled breakdown product is labelled deoxypyridinoline.

17. The method of claim 1 wherein the muscle tissue breakdown product is 3-methyl histidine, and said labelled breakdown product is labelled 3-methyl histidine.

18. A method for determining a plurality of tissue breakdown products, including breakdown products arising from at least one of connective tissue and muscle tissue, in a body fluid from an animal, comprising providing a standard comprising at least one of said breakdown products having an isotopic label, said label being radioactive or non-radioactive, combining a known quantity of said standard, containing a known quantity of said label, with a sample of the body fluid, substantially purifying from said combined standard and sample a breakdown product fraction containing labelled breakdown product from said standard together with breakdown products from the sample, and measuring the quantity of breakdown products and the quantity of label in the substantially purified breakdown product fraction, whereby the proportional difference between the quantity of label in the substantially purified breakdown product fraction and the known quantity of label in said known quantity of said standard provides a measure of the proportionate loss of breakdown products during the purifying step.

19. The method of claim 18 further comprising normalizing the quantity of measured substantially purified breakdown products to the quantity of creatinine present in the body fluid sample.

20. The method of claim 18 wherein said plurality of tissue breakdown products is selected from the group consisting of desmosine, isodesmosine, pyridinoline, deoxypyridinoline, and 3-methyl histidine.

21. The method of claim 18 wherein said standard is selected from the group consisting of desmosine, isodesmosine, pyridinoline, deoxypyridinoline, and 3-methyl histidine.

22. A method for assessing a condition of a selected connective tissue in a body fluid from an animal, comprising using the method of providing a standard comprising a breakdown product having an isotopic label, said label being radioactive or non-radioactive, combining a known quantity of said standard, containing a known quantity of said label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a connective tissue breakdown product in a body fluid from the animal, wherein the breakdown product is known to result from breakdown of the selected connective tissue.

23. The method of claim 22 wherein the selected connective tissue contains elastin.

24. The method of claim 22 wherein the selected connective tissue contains collagen.

25. A method for assessing a condition of a muscle tissue in a body fluid from an animal, comprising using the method of providing a standard comprising the breakdown product having an isotopic label, said label being radioactive or non-radioactive, combining a known quantity of said standard, containing a known quantity of said label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a muscle tissue breakdown product in a body fluid from the animal, wherein the breakdown product is known to result from breakdown of the muscle tissue.

26. A method for assessing a disease process that includes destruction of a specified tissue component, including at least one of a connective tissue component and a muscle tissue component, in a body fluid from an animal, comprising using the method of providing a standard comprising the breakdown product having an isotopic label, said label being a radioactive or non-radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a specified tissue breakdown product in a body fluid from the animal, wherein the breakdown product is known to result from breakdown of at least one of a specified connective tissue component and a specified muscle tissue component.

27. A method for assessing the efficacy of a therapy for treatment of a disease process that includes destruction of at least one of a specified connective tissue component and a specified muscle tissue component, in a body fluid from an animal, comprising using the method of providing a standard comprising the breakdown product having an isotopic label, said label being radioactive or non-radioactive, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining at least one of a connective tissue breakdown product and a muscle tissue breakdown product in a body fluid from the animal, wherein the breakdown product is known to result from breakdown of the specified tissue component.

28. The method of claim 27 wherein the disease process is chronic obstructive pulmonary disease.

29. The method of claim 27 wherein the disease process is cystic fibrosis.

30. The method of claim 27 wherein the disease process is autoimmune diseases such as rheumatoid arthritis and systemic lupus erythematosus.

31. The method of claim 27 wherein the disease process is osteoarthritis.

32. The method of claim 27 wherein the disease process is osteoporosis.

33. The method of claim 27 wherein the disease process is muscle atrophy.

34. The method of claim 27 wherein the disease process is sepsis.

35. The method of claim 27 wherein the disease process is scleroderma.

36. The method of claim 27 wherein the disease process is lung emphysema due to a genetic deficiency of alpha-1-antitrypsin.

37. The method of claim 27 wherein the disease process is a normal process of pregnancy.

38. The method of claim 27 wherein the disease process is an abnormal process of impending premature termination of pregnancy.

39. The method of claim 27 wherein the disease process is fibrosis of the lung.

40. The method of claim 27 wherein the disease process is fibrosis of the liver.

41. The method of claim 27 wherein the disease process is inflammation of the blood vessels.

42. The method of claim 27 wherein the disease process is atherosclerosis.

43. The method of claim 27 wherein the disease process is a cancerous growth.

* * * * *

UNITED STATES PATENT AND TRADEMARK OFFICE
CERTIFICATE OF CORRECTION

PATENT NO. : 5,354,662
DATED      : October 11, 1994
INVENTOR(S) : Phillip J. Stone, et. al.

It is certified that error appears in the above-indentified patent and that said Letters Patent is hereby corrected as shown below:

Column 13, line 27, delete "dearly" and insert therefor-- nearly--.

Signed and Sealed this

Thirteenth Day of December, 1994

Attest:

BRUCE LEHMAN

*Attesting Officer*          *Commissioner of Patents and Trademarks*